US009265415B1

(12) United States Patent
Starner et al.

(10) Patent No.: US 9,265,415 B1
(45) Date of Patent: Feb. 23, 2016

(54) INPUT DETECTION

(71) Applicant: Google Inc., Mountain View, CA (US)

(72) Inventors: Thad Eugene Starner, Mountain View, CA (US); Bo Wu, Alhambra, CA (US); Yong Zhao, San Jose, CA (US)

(73) Assignee: Google Inc., Mountain View, CA (US)

( * ) Notice: Subject to any disclaimer, the term of this patent is extended or adjusted under 35 U.S.C. 154(b) by 138 days.

(21) Appl. No.: 13/631,333

(22) Filed: Sep. 28, 2012

Related U.S. Application Data

(60) Provisional application No. 61/584,169, filed on Jan. 6, 2012.

(51) Int. Cl.
*A61B 3/14* (2006.01)
*A61B 3/113* (2006.01)

(52) U.S. Cl.
CPC .. *A61B 3/113* (2013.01); *A61B 3/14* (2013.01)

(58) Field of Classification Search
CPC .......... A61B 3/113; A61B 3/103; A61B 3/14; A61B 3/1208; A61B 3/1225; G02B 27/0103; G02B 27/0172; G02B 27/0149
USPC ......... 351/205, 206, 209, 210, 220, 221, 246; 359/13, 630, 632; 382/103, 190, 291
See application file for complete search history.

(56) References Cited

U.S. PATENT DOCUMENTS

| | | | | |
|---|---|---|---|---|
| 7,306,337 B2* | 12/2007 | Ji et al. | | 351/209 |
| 7,809,160 B2* | 10/2010 | Vertegaal et al. | | 382/103 |
| 2010/0189354 A1* | 7/2010 | de Campos et al. | | 382/190 |
| 2010/0295769 A1* | 11/2010 | Lundstrom | | 345/156 |
| 2011/0182472 A1* | 7/2011 | Hansen | | 382/103 |

* cited by examiner

*Primary Examiner* — Thomas K Pham
*Assistant Examiner* — Jie Lei
(74) *Attorney, Agent, or Firm* — McDonnell Boehnen Hulbert & Berghoff LLP

(57) ABSTRACT

Methods and systems that are described herein may help to dynamically utilize multiple eye-tracking techniques to more accurately determine eye position and/or eye movement. An exemplary system may be configured to: (a) perform at least a first and a second eye-tracking process; (b) determine a reliability indication for at least one of the eye-tracking processes; (c) determine a respective weight for each of the eye-tracking processes based at least in part on the reliability indication; (d) determine a combined eye position based on a weighted combination of eye-position data from the two or more eye-tracking processes, wherein the eye-position data from each eye-tracking process is weighted by the respectively determined weight for the eye-tracking process; and (e) carry out functions based on the combined eye position.

22 Claims, 19 Drawing Sheets

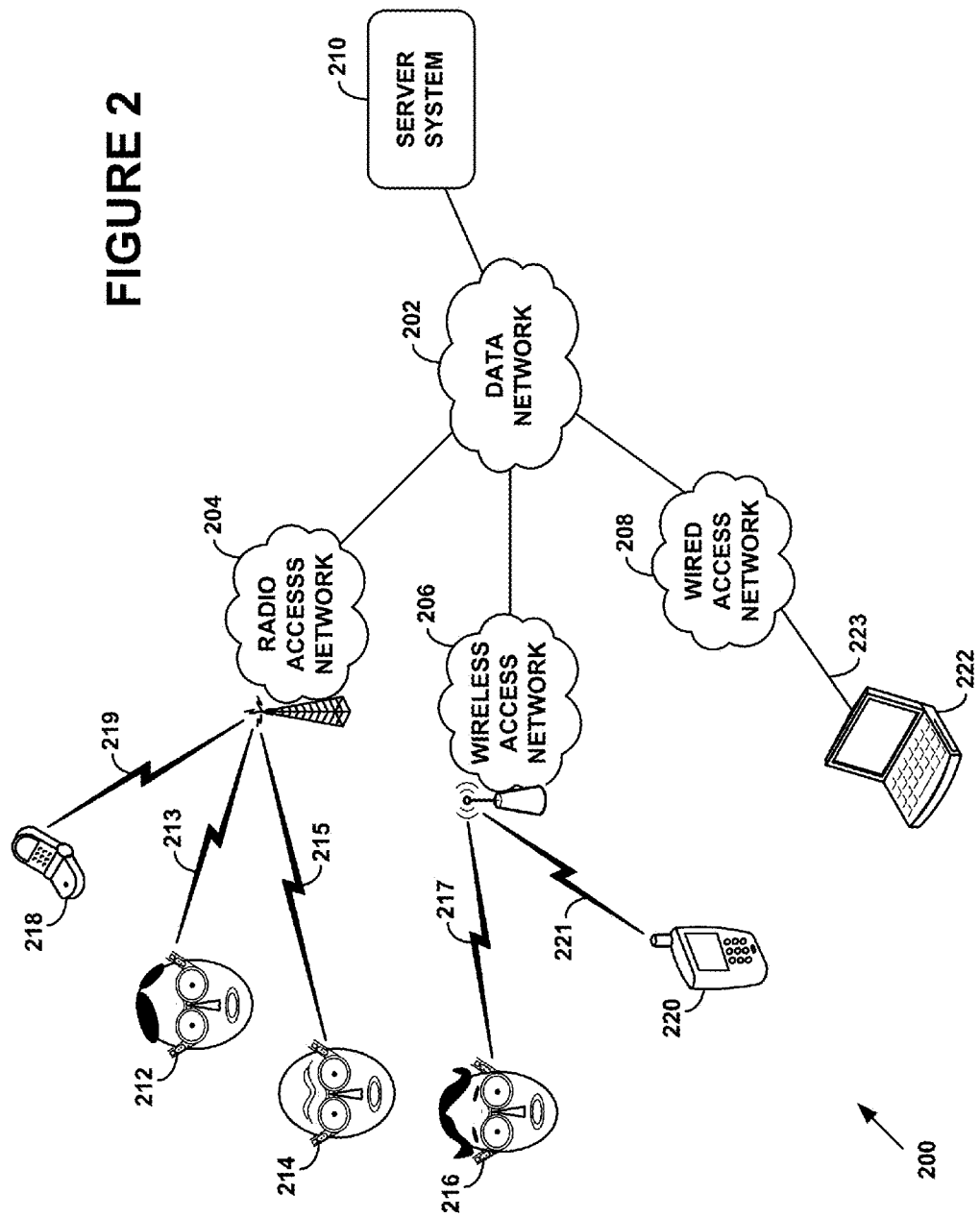

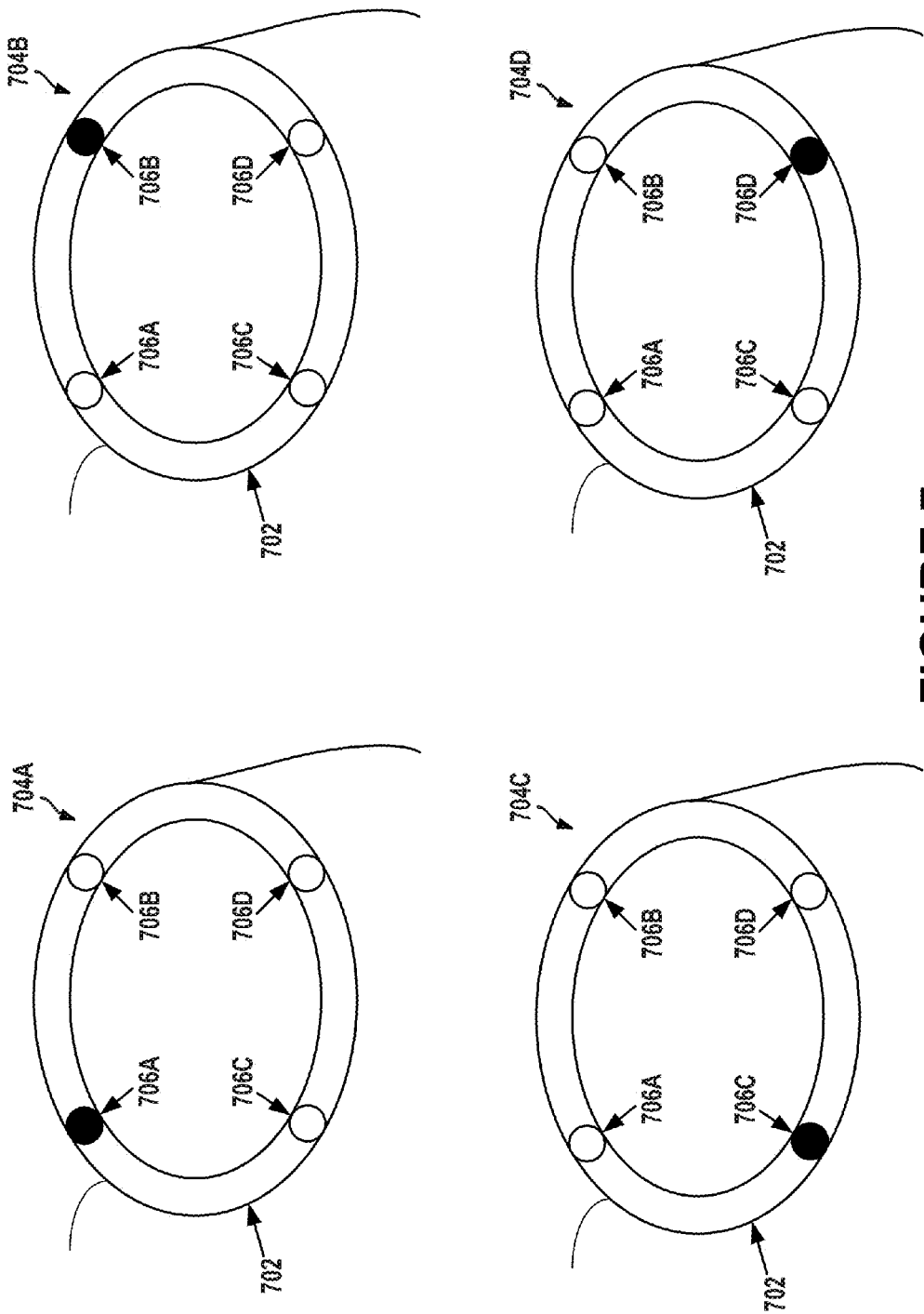

INPUT DETECTION

CROSS REFERENCE TO RELATED APPLICATION

This patent application claims priority to U.S. Application No. 61/584,169, filed Jan. 6, 2012, the contents of which are entirely incorporated herein by reference, as if fully set forth in this application.

BACKGROUND

Unless otherwise indicated herein, the materials described in this section are not prior art to the claims in this application and are not admitted to be prior art by inclusion in this section.

Computing devices such as personal computers, laptop computers, tablet computers, cellular phones, and countless types of Internet-capable devices are increasingly prevalent in numerous aspects of modern life. Over time, the manner in which these devices are providing information to users is becoming more intelligent, more efficient, more intuitive, and/or less obtrusive.

The trend toward miniaturization of computing hardware, peripherals, as well as of sensors, detectors, and image and audio processors, among other technologies, has helped open up a field sometimes referred to as "wearable computing." In the area of image and visual processing and production, in particular, it has become possible to consider wearable displays that place a very small image display element close enough to a wearer's (or user's) eye(s) such that the displayed image fills or nearly fills the field of view, and appears as a normal sized image, such as might be displayed on a traditional image display device. The relevant technology may be referred to as "near-eye displays."

Near-eye displays are fundamental components of wearable displays, also sometimes called "head-mounted displays" (HMDs). A head-mounted display places a graphic display or displays close to one or both eyes of a wearer. To generate the images on a display, a computer processing system may be used. Such displays may occupy a wearer's entire field of view, or only occupy part of wearer's field of view. Further, head-mounted displays may be as small as a pair of glasses or as large as a helmet.

Emerging and anticipated uses of wearable displays include applications in which users interact in real time with an augmented or virtual reality. Such applications can be mission-critical or safety-critical, such as in a public safety or aviation setting. The applications can also be recreational, such as interactive gaming.

SUMMARY

In one aspect, an exemplary computer-implemented method involves: (a) carrying out at least one of two or more eye-tracking processes that provide eye-position data, wherein the two or more eye-tracking processes comprise at least a first and a second eye-tracking process; (b) determining a reliability indication for at least one of the eye-tracking processes; (c) determining a respective weight for each of the eye-tracking processes based at least in part on the reliability indication; (d) determining a combined eye position based on a weighted combination of eye-position data from the two or more eye-tracking processes, wherein the eye-position data from each eye-tracking process is weighted by the respectively determined weight for the eye-tracking process; and (e) instructing a computing device to utilize the combined eye position for one or more functions that incorporate eye-position data.

In another aspect an exemplary system may include a non-transitory computer-readable medium and program instructions that are stored on the non-transitory computer-readable medium. The program instructions may be executable by at least one processor to: (a) perform two or more eye-tracking processes to determine eye-position data, wherein the two or more eye-tracking processes comprise at least a first and a second eye-tracking process; (b) determine a reliability indication for at least one of the eye-tracking processes; (c) determine a respective weight for each of the eye-tracking processes based at least in part on the reliability indication; (d) determine a combined eye position based on a weighted combination of eye-position data from the two or more eye-tracking processes, wherein the eye-position data from each eye-tracking process is weighted by respectively determined weight for the eye-tracking process; and (e) instruct a computing device to carry out functions based on the combined eye position.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2 is a simplified illustration of a network via which one or more devices may engage in communications, according to an exemplary embodiment.

FIG. 7 is a simplified illustration of a predetermined sequence of light-source combinations, according to an exemplary embodiment.

DETAILED DESCRIPTION

Figure 1A:
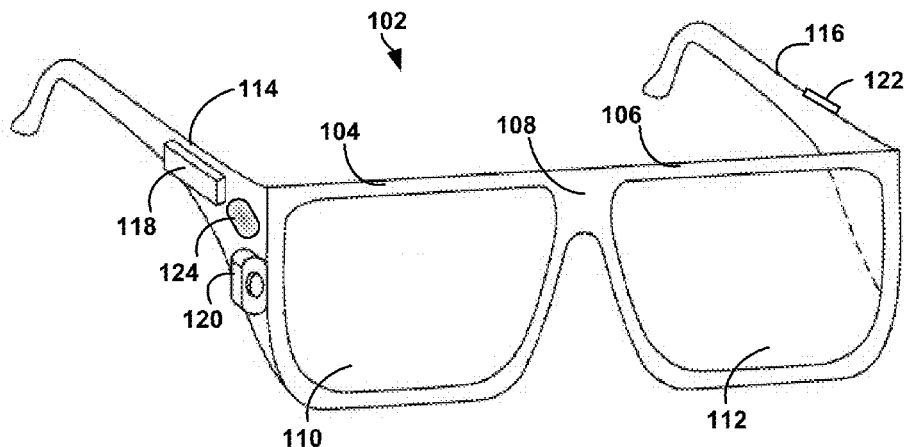
FIG. 1A illustrates a wearable computing system according to an exemplary embodiment.

Exemplary methods and systems are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

I. Overview

Exemplary embodiments may be implemented by or in association with a computing device that includes or takes the form of a head-mounted display (HMD). In particular, an exemplary computing system may be configured for two or more different types of eye- or gaze-tracking processes. To facilitate various eye-tracking processes, an HMD may include an inward-facing camera or cameras that is/are configured to capture images of the wearer's eye or eyes (the images may be video and/or still images). The combination of the inward-facing camera and the cornea may act as a catadioptric (mirror+lens) imaging system that is referred to as the "corneal imaging system." This corneal imaging system may therefore capture images of the eye. These images of the eye may be utilized in various techniques for determining eye position and/or eye movement.

In an exemplary embodiment, the wearable computer may intelligently switch between use of a number of different eye-tracking processes and/or use of various combinations of eye-tracking processes to help provide more accurate eye-tracking data. For example, an exemplary wearable computer may be configured for: (1) eye-tracking based on controlled glints, (2) limbus tracking, (3) eye-tracking based on ambient (i.e., uncontrolled) glints, (4) pupil tracking, (5) eye-tracking with inward-facing proximity sensors. Other eye-tracking techniques are also possible.

In some embodiments, a computing device may dynamically switch between different eye-tracking processes, but use only one eye-tracking process at a given point in time. For example, a computing device may determine eye position using two different processes, and dynamically select the calculation from the method that is deemed to be most accurate. Other examples are possible. In other embodiments, a computing device may use a combination of eye-tracking processes to help provide more accurate eye-tracking data, weighing calculating an eye-position by placing a certain weight on the data from each of the processes.

In some implementations, a wearable computer may be configured to utilize both (a) eye-tracking based on controlled glints in a retinal image and (b) limbus tracking. In such an implementation, the wearable computer may switch between controlled glints and limbus tracking in a binary manner, using data from one process at a time. However, the wearable computer may also use data from both processes, weighting the data from each process based on factors that are indicative of the reliability/accuracy of the process.

In other implementations, a wearable computer may be configured to utilize (a) eye-tracking based on controlled glints in a retinal image, (b) limbus tracking, and (c) eye-tracking based on ambient glints in a retinal image. In such an implementation, the wearable computer may switch between controlled glints, limbus tracking, and eye-tracking in a binary manner, using eye-position estimation(s) from one process at a time. However, the wearable computer may also use data from all the process or a subset of the processes, weighting the data from each process based on factors that are indicative of the reliability/accuracy of the given process.

In some embodiments, eye-tracking processes may be weighted so as to take into account that using ambient glints may be more difficult and/or less reliable than using controlled glints and/or limbus tracking. Accordingly, when controlled glints are producing reliable data (e.g., when the majority controlled glints are positively identified from frame to frame), a wearable computer may ignore ambient glints or reduce the weight given to data based on ambient lights. Similarly, when limbus tracking is producing reliable data (e.g., when the circular outline of the limbus can be identified), the wearable computer may ignore or reduce the weight given to ambient glints.

However, a wearable computer may also switch to ambient glints exclusively, or weight eye-position data that is based on ambient glints more heavily, when it determines that reflections of ambient light are obscuring controlled glints in the retinal image and/or making it difficult to identify the circular outline of the limbus in the retinal image. Other examples are also possible.

In a further aspect of some embodiments, the wearable computer may weight limbus tracking according to how much of the circular outline of the limbus can be identified in the retinal image. For instance, if ambient lights are obscuring the outline of the limbus, then the wearable computer may reduce the weight given to limbus-tracking data, or might even ignore limbus tracking altogether.

Various other techniques may also be used to weight data from the eye-tracking processes. For instance, in some embodiments, a Kalman filter may be applied to weight the data produced by the various eye-tracking methods and output a combined eye-tracking signal. However, other techniques for weighting and/or combining data from concurrent eye-tracking processes may also be utilized. For example, eye-tracking data may be determined by weighting the eye-position determined by each process individually, and then adding the weighted eye-positions (i.e., determining a weighted average of the results from the various eye-tracking processes).

II. Exemplary Systems

Systems and devices in which exemplary embodiments may be implemented will now be described in greater detail.

In general, an exemplary system may be implemented in or may take the form of a wearable computer. In particular, an exemplary system may be implemented in association with or take the form of a head-mountable display (HMD), or a computing system that receives data from an HMD, such as a cloud-based server system.

However, an exemplary system may also be implemented in or take the form of other devices, such as a mobile phone, among others. Further, an exemplary system may take the form of non-transitory computer readable medium, which has program instructions stored thereon that are executable by at a processor to provide the functionality described herein. An exemplary system may also take the form of a device such as a wearable computer or mobile phone, or a subsystem of such a device, which includes such a non-transitory computer readable medium having such program instructions stored thereon.

FIG. 1A illustrates a wearable computing system according to an exemplary embodiment. In FIG. 1A, the wearable computing system takes the form of a head-mounted device (HMD) 102 (which may also be referred to as a head-mounted display). It should be understood, however, that exemplary systems and devices may take the form of or be implemented within or in association with other types of devices, without departing from the scope of the invention. As illustrated in FIG. 1A, the head-mounted device 102 comprises frame elements including lens-frames 104, 106 and a center frame support 108, lens elements 110, 112, and extending side-arms 114, 116. The center frame support 108 and the extending side-arms 114, 116 are configured to secure the head-mounted device 102 to a user's face via a user's nose and ears, respectively.

Each of the frame elements 104, 106, and 108 and the extending side-arms 114, 116 may be formed of a solid structure of plastic and/or metal, or may be formed of a hollow structure of similar material so as to allow wiring and component interconnects to be internally routed through the head-mounted device 102. Other materials may be possible as well.

One or more of each of the lens elements 110, 112 may be formed of any material that can suitably display a projected image or graphic. Each of the lens elements 110, 112 may also be sufficiently transparent to allow a user to see through the lens element. Combining these two features of the lens elements may facilitate an augmented reality or heads-up display where the projected image or graphic is superimposed over a real-world view as perceived by the user through the lens elements.

The extending side-arms 114, 116 may each be projections that extend away from the lens-frames 104, 106, respectively, and may be positioned behind a user's ears to secure the head-mounted device 102 to the user. The extending side-arms 114, 116 may further secure the head-mounted device 102 to the user by extending around a rear portion of the user's head. Additionally or alternatively, for example, the HMD 102 may connect to or be affixed within a head-mounted helmet structure. Other possibilities exist as well.

The HMD 102 may also include an on-board computing system 118, a video camera 120, a sensor 122, and a finger-operable touch pad 124. The on-board computing system 118 is shown to be positioned on the extending side-arm 114 of the head-mounted device 102; however, the on-board computing system 118 may be provided on other parts of the head-mounted device 102 or may be positioned remote from the head-mounted device 102 (e.g., the on-board computing system 118 could be wire- or wirelessly-connected to the head-mounted device 102). The on-board computing system 118 may include a processor and memory, for example. The on-board computing system 118 may be configured to receive and analyze data from the video camera 120 and the finger-operable touch pad 124 (and possibly from other sensory devices, user interfaces, or both) and generate images for output by the lens elements 110 and 112.

The video camera 120 is shown positioned on the extending side-arm 114 of the head-mounted device 102; however, the video camera 120 may be provided on other parts of the head-mounted device 102. The video camera 120 may be configured to capture images at various resolutions or at different frame rates. Many video cameras with a small form-factor, such as those used in cell phones or webcams, for example, may be incorporated into an example of the HMD 102.

Further, although FIG. 1A illustrates one video camera 120, more video cameras may be used, and each may be configured to capture the same view, or to capture different views. For example, the video camera 120 may be forward facing to capture at least a portion of the real-world view perceived by the user. This forward facing image captured by the video camera 120 may then be used to generate an augmented reality where computer generated images appear to interact with the real-world view perceived by the user.

The sensor 122 is shown on the extending side-arm 116 of the head-mounted device 102; however, the sensor 122 may be positioned on other parts of the head-mounted device 102. The sensor 122 may include one or more of a gyroscope or an accelerometer, for example. Other sensing devices may be included within, or in addition to, the sensor 122 or other sensing functions may be performed by the sensor 122.

The finger-operable touch pad 124 is shown on the extending side-arm 114 of the head-mounted device 102. However, the finger-operable touch pad 124 may be positioned on other parts of the head-mounted device 102. Also, more than one finger-operable touch pad may be present on the head-mounted device 102. The finger-operable touch pad 124 may be used by a user to input commands. The finger-operable touch pad 124 may sense at least one of a position and a movement of a finger via capacitive sensing, resistance sensing, or a surface acoustic wave process, among other possibilities. The finger-operable touch pad 124 may be capable of sensing finger movement in a direction parallel or planar to the pad surface, in a direction normal to the pad surface, or both, and may also be capable of sensing a level of pressure applied to the pad surface. The finger-operable touch pad 124 may be formed of one or more translucent or transparent insulating layers and one or more translucent or transparent conducting layers. Edges of the finger-operable touch pad 124 may be formed to have a raised, indented, or roughened surface, so as to provide tactile feedback to a user when the user's finger reaches the edge, or other area, of the finger-operable touch pad 124. If more than one finger-operable touch pad is present, each finger-operable touch pad may be operated independently, and may provide a different function.

Figure 1B:
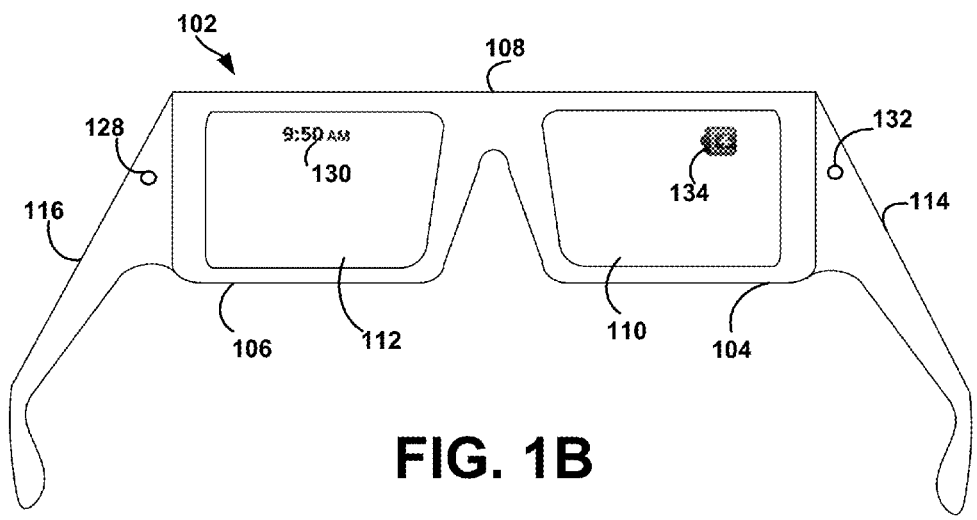
FIG. 1B illustrates an alternate view of the wearable computing device illustrated in FIG. 1A.

FIG. 1B illustrates an alternate view of the wearable computing device illustrated in FIG. 1A. As shown in FIG. 1B, the lens elements 110, 112 may act as display elements. The head-mounted device 102 may include a first projector 128 coupled to an inside surface of the extending side-arm 116 and configured to project a display 130 onto an inside surface of the lens element 112. Additionally or alternatively, a second projector 132 may be coupled to an inside surface of the extending side-arm 114 and configured to project a display 134 onto an inside surface of the lens element 110.

The lens elements 110, 112 may act as a combiner in a light projection system and may include a coating that reflects the light projected onto them from the projectors 128, 132. In some embodiments, a reflective coating may not be used (e.g., when the projectors 128, 132 are scanning laser devices).

Although not explicitly shown in the figures, the HMD could include an eye-tracking system or a portion of such a system. In an exemplary embodiment, the HMD could include inward- or rearward-facing (i.e., eye-facing) light source(s) and/or camera(s) to facilitate eye-tracking functions. For example, an HMD may include inward-facing light sources, such as an LED(s), at generally known location(s) with respect to one another and/or with respect to an eye under observation. The inward-facing camera may therefore capture images that include the reflections of the light source(s) off the eye; or in other words, images that capture the controlled glints that correspond to the inward-facing light sources. As such, the positioning of the controlled glints in given image may be indicative of the position of the eye at the time the image was captured.

In a further aspect, with the above configuration, successive video frames may capture movement of the controlled in the image plane as the one or more eyes move. Thus, with the relative geometry of the controlled light source and the one or more eyes known, the observed movement of the controlled glints in the image plane may be analyzed in order to measure the movement of the eye.

In alternative embodiments, other types of display elements may also be used. For example, the lens elements 110, 112 themselves may include: a transparent or semi-transparent matrix display, such as an electroluminescent display or a liquid crystal display, one or more waveguides for delivering an image to the user's eyes, or other optical elements capable of delivering an in focus near-to-eye image to the user. A corresponding display driver may be disposed within the frame elements 104, 106 for driving such a matrix display. Alternatively or additionally, a laser or LED source and scanning system could be used to draw a raster display directly onto the retina of one or more of the user's eyes. Other possibilities exist as well.

While the wearable computing system 100 of the example embodiment illustrated in FIGS. 1a and 1b is configured as a unified package, integrated in the HMD component, other configurations are possible as well. For example, although not explicitly shown in FIGS. 1a and 1b, the wearable computing system 100 could be implemented in a distributed architecture in which all or part of the on-board computing system 118 is configured remotely from the eyeglasses 102. For example, some or all of the on-board computing system 118 could be made wearable in or on clothing as an accessory, such as in a garment pocket or on a belt clip. Similarly, other components depicted in FIGS. 1a and/or 1b as integrated in the eyeglasses 102 could also be configured remotely from the HMD component. In such a distributed architecture, certain components might still be integrated in HMD component. For instance, one or more sensors (e.g., a magnetometer, gyroscope, etc.) could be integrated in eyeglasses 102.

In an example distributed configuration, the HMD component (including other integrated components) could communicate with remote components via the communication interface 126 (or via a dedicated connection, distinct from the communication interface 126). By way of example, a wired (e.g. USB or Ethernet) or wireless (e.g., WiFi or Bluetooth) connection could support communications between a remote computing system and a HMD component. Additionally, such a communication link could be implemented between a HMD component and other remote devices, such as a laptop computer or a mobile telephone, for instance.

Figure 1C:
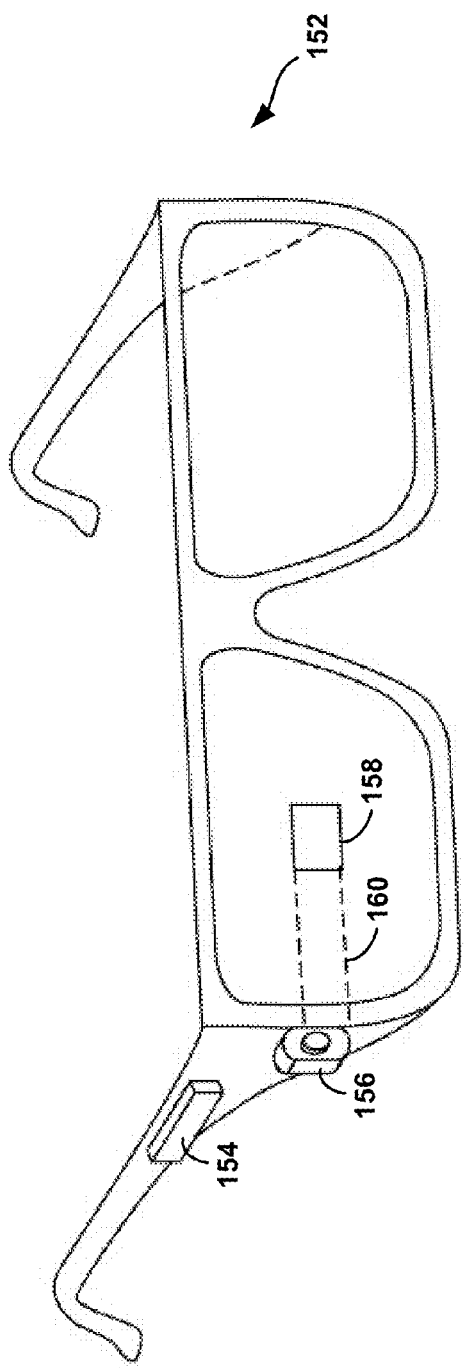
FIG. 1C illustrates another wearable computing system according to an exemplary embodiment.

FIG. 1C illustrates another wearable computing system according to an exemplary embodiment, which takes the form of an HMD 152. The HMD 152 may include frame elements and side-arms such as those described with respect to FIGS. 1A and 1B. The HMD 152 may additionally include an on-board computing system 154 and a video camera 156, such as those described with respect to FIGS. 1A and 1B. The video camera 156 is shown mounted on a frame of the HMD 152. However, the video camera 156 may be mounted at other positions as well.

As shown in FIG. 1C, the HMD 152 may include a single display 158 which may be coupled to the device. The display 158 may be formed on one of the lens elements of the HMD 152, such as a lens element described with respect to FIGS. 1A and 1B, and may be configured to overlay computer-generated graphics in the user's view of the physical world. The display 158 is shown to be provided in a center of a lens of the HMD 152, however, the display 158 may be provided in other positions. The display 158 is controllable via the computing system 154 that is coupled to the display 158 via an optical waveguide 160.

Figure 1D:
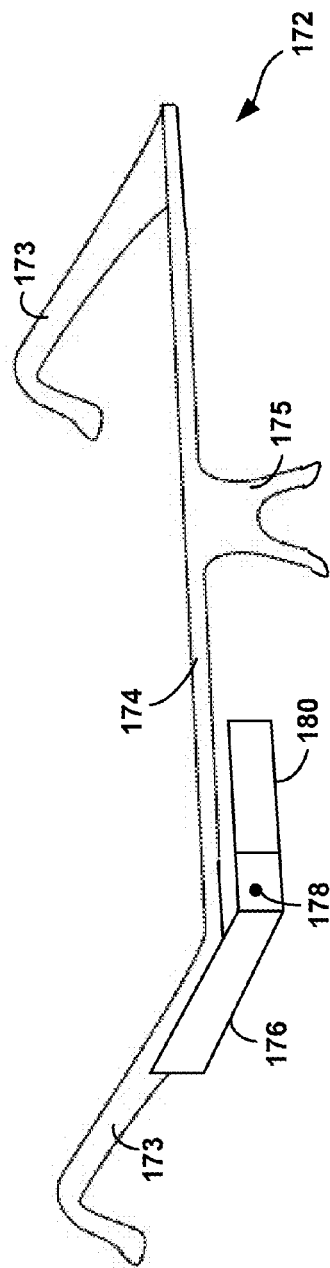
FIG. 1D illustrates another wearable computing system according to an exemplary embodiment.

FIG. 1D illustrates another wearable computing system according to an exemplary embodiment, which takes the form of an HMD 172. The HMD 172 may include side-arms 173, a center frame support 174, and a bridge portion with nose-piece 175. In the example shown in FIG. 1D, the center frame support 174 connects the side-arms 173. The HMD 172 does not include lens-frames containing lens elements. The HMD 172 may additionally include an on-board computing system 176 and a video camera 178, such as those described with respect to FIGS. 1A and 1B.

The HMD 172 may include a single lens element 180 that may be coupled to one of the side-arms 173 or the center frame support 174. The lens element 180 may include a display such as the display described with reference to FIGS. 1A and 1B, and may be configured to overlay computer-generated graphics upon the user's view of the physical world. In one example, the single lens element 180 may be coupled to the inner side (i.e., the side exposed to a portion of a user's head when worn by the user) of the extending side-arm 173. The single lens element 180 may be positioned in front of or proximate to a user's eye when the HMD 172 is worn by a user. For example, the single lens element 180 may be positioned below the center frame support 174, as shown in FIG. 1D.

FIG. 2 illustrates one view of a network 200 via which one or more HMDs and/or other types of computing devices, such as those illustrated in FIGS. 1A-1D, could engage in communications. As depicted, the network 200 includes a data network 202 that is connected to each of a radio access network (RAN) 204, a wireless access network 206, and a wired access network 208. The data network 202 could represent the one or more interconnected communication networks, such as or including the Internet. The radio access network 204 could represent a service provider's cellular radio network supporting, for instance, 3G and/or 4G cellular radio technologies (e.g., CDMA, EVDO, GSM, UMTS, LTE, WiMAX). The wireless access network 206 could represent a residential or hot-spot wireless area network supporting, such as, Bluetooth, ZigBee, and WiFi (e.g., 802.11a, 802.11b, 802.11g). The wired access network 208 could represent a residential or commercial local area network supporting, for instance, Ethernet.

The network 200 also includes a server system 210 connected to the data network 202. The server system 210 could represent a website or other network-based facility for providing one or another type of service to users. For instance, in accordance with an example embodiment, the server system 210 could host an online social networking service or website. As another example, the server system 210 could provide a network-based information search service. As still a further example, the server system 210 could receive eye-tracking data from a HMD, and returned analyzed results to the HMD.

FIG. 2 also shows various end-user and/or client devices connected to the network 200 via one of the three access networks. By way of example, an HMD 212 is connected to the RAN 204 via an air interface 213 (e.g., a 3G or 4G technology), and an HMD 214 is connected to the RAN 204 via an air interface 215 (e.g., a 3G or 4G technology). Also by way of example, an HMD 216 is connected to the wireless access network 206 via an air interface 217 (e.g., a WiFi technology). In addition and also by way of example, a mobile phone 218 is shown connected to the RAN 204 via an air interface 219, a smart phone 220 is shown connected to the wireless access network 206 via an air interface 221, and a laptop computer 222 is shown connected to the wired access network 208 via a wired interface 223. Each of the end-user devices could communicate with one or another network-connected device via its respective connection with the network. It could be possible as well for some of these end-user devices to communicate directly with each other (or other end-user devices not shown).

Each of the HMDs 212, 214, and 216 is depicted as being worn by different user (each user being represented by a cartoon face) in order to signify possible user-related variables, circumstances, and applications that may be associated with each HMD. For instance, the HMD 212 could at one time upload content to an online social networking service, whereas the HMD 214 could at the same or another time send a request to a network-based information search service. Users could interact with each other and/or with the network via their respective HMDs. Other examples are possible as well. For the purposes of most of the discussion herein it is usually sufficient to reference only an HMD without referencing the user (or wearer) the HMD. Explicit reference to or discussion of a user (or wearer) of an HMD will be made as necessary.

Figure 3A:
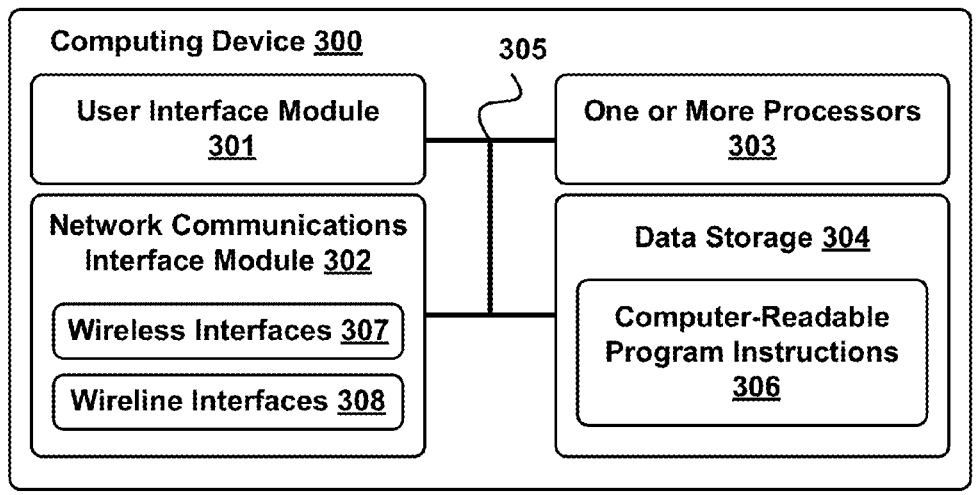
FIG. 3A is a block diagram of a computing device 300 in accordance with an exemplary embodiment.
Figure 3B:
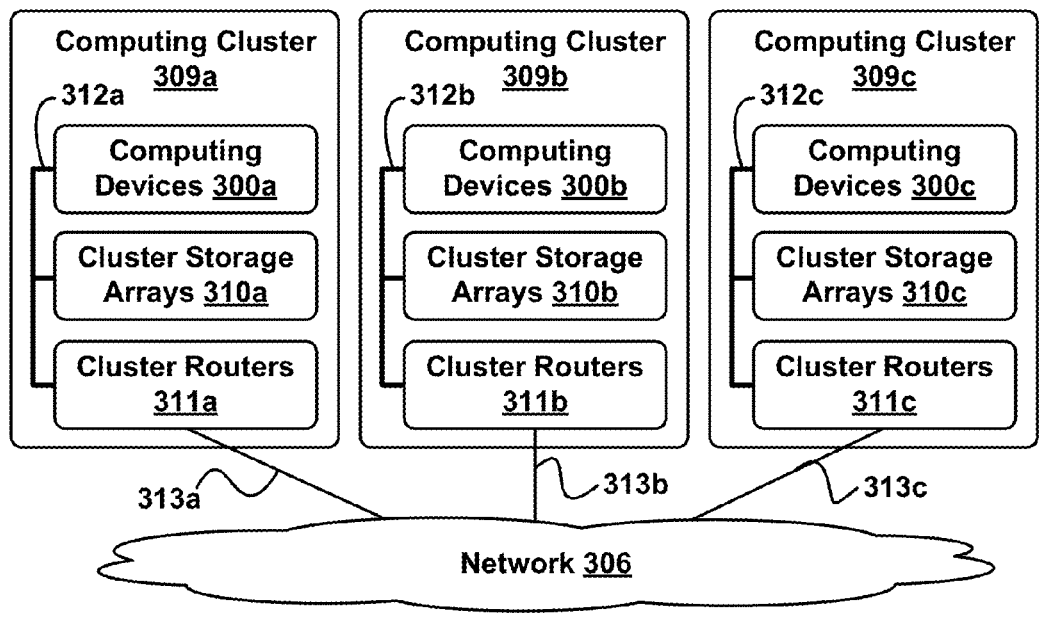
FIG. 3B depicts a network with computing clusters in accordance with an example embodiment.

A network server, such as the server system 210 in FIG. 2, could take various forms and be implemented in one or more different ways. FIGS. 3a and 3b illustrate two example embodiments of a server system: an integrated system including a representative computing device (FIG. 3a), and a distributed system (FIG. 3b) including multiple representative computing devices, as well as additional system elements, communicatively connected together.

FIG. 3a is a block diagram of a computing device 300 in accordance with an example embodiment. As shown, computing device 300 includes a user interface module 301, a network-communication interface module 302, one or more processors 303, and data storage 304, all of which can be linked together via a system bus, network, or other connection mechanism 305. The computing device 300 may be any type of device that can receive data and provide information for display in association with the received data. For example, the device 300 may take the form of or be included as part of a wearable computing device, such as the head-mounted devices 102, 152, or 172 described with reference to FIGS. 1A-1D. Further, as noted above, computing device 300 could also take the form of or be included in an integrated server system. Computing device 300 may take other forms and/or be included as part of other systems as well.

The user interface module 301 can be operable to send data to and/or receive data from external user input/output devices. For example, the user interface module 301 can be configured to send/receive data to/from user input devices such as a keyboard, a keypad, a touch screen, a computer mouse, a track ball, a joystick, and/or other similar devices, now known or later developed. The user interface module 301 can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interface module 301 can also be configured to generate audible output(s), such as a speaker, speaker jack, audio output port, audio output device, earphones, and/or other similar devices, now known or later developed.

The network-communications interface module 302 can include one or more wireless interfaces 307 and/or wireline interfaces 308 that are configurable to communicate via a network, such as the network 202 shown in FIG. 2. The wireless interfaces 307 can include one or more wireless transceivers, such as a Bluetooth transceiver, a Wi-Fi transceiver perhaps operating in accordance with an IEEE 802.11 standard (e.g., 802.11a, 802.11b, 802.11g), a WiMAX transceiver perhaps operating in accordance with an IEEE 802.16 standard, and/or other types of wireless transceivers configurable to communicate via a wireless network. The wireline interfaces 308 can include one or more wireline transceivers, such as an Ethernet transceiver, a Universal Serial Bus (USB) transceiver, or similar transceiver configurable to communicate via a wire, a twisted pair of wires, a coaxial cable, an optical link, a fiber-optic link, or other physical connection to a wireline network.

In some embodiments, the network communications interface module 302 can be configured to provide reliable, secured, compressed, and/or authenticated communications. For each communication described herein, information for ensuring reliable communications (e.g., guaranteed message delivery) can be provided, perhaps as part of a message header and/or footer (e.g., packet/message sequencing information, encapsulation header(s) and/or footer(s), size/time information, and transmission verification information such as cyclic redundancy check (CRC) and/or parity check values). Communications can be compressed and decompressed using one or more compression and/or decompression algorithms and/or protocols such as, but not limited to, one or more lossless data compression algorithms and/or one or more lossy data compression algorithms. Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well or in addition to those listed herein to secure (and then decrypt/decode) communications.

The one or more processors 303 can include one or more general purpose processors and/or one or more special purpose processors (e.g., digital signal processors, application specific integrated circuits, etc.). The one or more processors 303 can be configured to execute computer-readable program instructions 306 that are contained in the data storage 304 and/or other instructions as described herein.

The data storage 304 can include one or more computer-readable storage media that can be read or accessed by at least one of the processors 303. The one or more computer-readable storage media can include volatile and/or non-volatile storage components, such as optical, magnetic, organic or other memory or disc storage, which can be integrated in whole or in part with at least one of the one or more processors 303. In some embodiments, the data storage 304 can be implemented using a single physical device (e.g., one optical, magnetic, organic or other memory or disc storage unit), while in other embodiments, the data storage 304 can be implemented using two or more physical devices.

Computer-readable storage media associated with data storage 304 and/or other computer-readable media described herein can also include non-transitory computer-readable media such as computer-readable media that stores data for short periods of time like register memory, processor cache, and random access memory (RAM). Computer-readable storage media associated with data storage 304 and/or other computer-readable media described herein can also include non-transitory computer readable media that stores program code and/or data for longer periods of time, such as secondary or persistent long term storage, like read only memory (ROM), optical or magnetic disks, compact-disc read only memory (CD-ROM), for example. Computer-readable storage media associated with data storage 304 and/or other computer-readable media described herein can also be any other volatile or non-volatile storage systems. Computer-readable storage media associated with data storage 304 and/or other computer-readable media described herein can be considered computer readable storage media for example, or a tangible storage device.

The data storage 304 can include computer-readable program instructions 306 and perhaps additional data. In some embodiments, the data storage 304 can additionally include storage required to perform at least part of the herein-described techniques, methods, and/or at least part of the functionality of the herein-described devices and networks.

FIG. 3b depicts a network 306 with computing clusters 309a, 309b, and 309c in accordance with an example embodiment. In FIG. 3b, functions of a network server, such as the server system 210 in FIG. 2, can be distributed among three computing clusters 309a, 309b, and 308c. The computing cluster 309a can include one or more computing devices 300a, cluster storage arrays 310a, and cluster routers 311a, connected together by local cluster network 312a. Similarly, computing cluster 309b can include one or more computing devices 300b, cluster storage arrays 310b, and cluster routers 311b, connected together by local cluster network 312b. Likewise, computing cluster 309c can include one or more computing devices 300c, cluster storage arrays 310c, and cluster routers 311c, connected together by a local cluster network 312c.

In some embodiments, each of computing clusters 309a, 309b, and 309c can have an equal number of computing devices, an equal number of cluster storage arrays, and an equal number of cluster routers. In other embodiments, however, some or all of computing clusters 309a, 309b, and 309c can have different numbers of computing devices, different numbers of cluster storage arrays, and/or different numbers of cluster routers. The number of computing devices, cluster storage arrays, and cluster routers in each computing cluster can depend on the computing task or tasks assigned to each computing cluster.

Cluster storage arrays 310a, 310b, and 310c of computing clusters 309a, 309b, and 309c can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

The cluster routers 311a, 311b, and 311c in the computing clusters 309a, 309b, and 309c can include networking equipment configured to provide internal and external communications for the computing clusters. For example, the cluster routers 311a in the computing cluster 309a can include one or more internet switching and/or routing devices configured to provide (i) local area network communications between the computing devices 300a and the cluster storage arrays 301a via the local cluster network 312a, and/or (ii) wide area network communications between the computing cluster 309a and the computing clusters 309b and 309c via the wide area network connection 313a to the network 306. The cluster routers 311b and 311c can include network equipment similar to the cluster routers 311a, and the cluster routers 311b and 311c can perform similar networking functions for the computing clusters 309b and 309b that the cluster routers 311a perform for the computing cluster 309a.

III. Exemplary Methods

Figure 4:
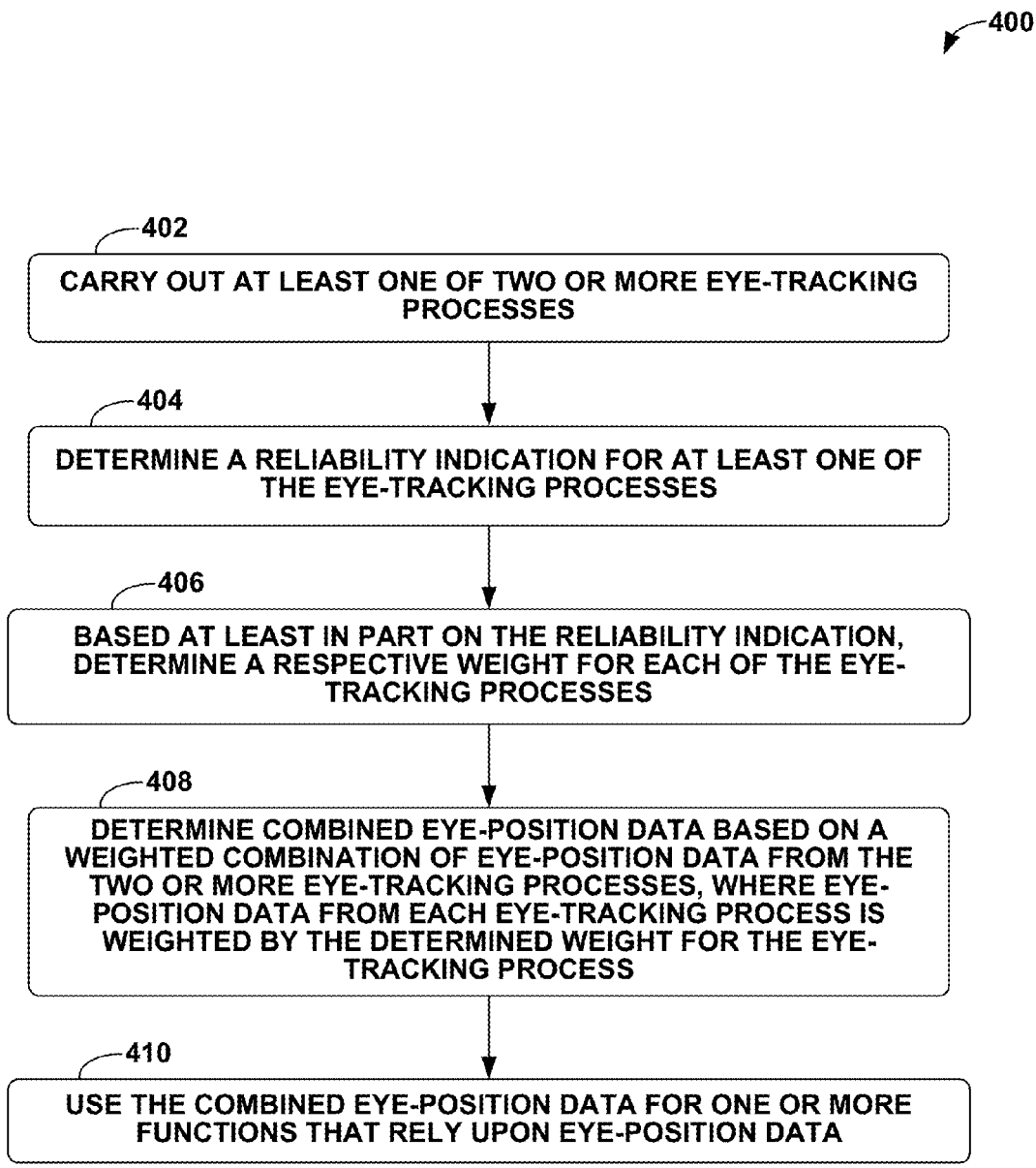
FIG. 4 is a flow chart illustrating a method, according to an exemplary embodiment.

FIG. 4 is a flow chart illustrating a method 400, according to an exemplary embodiment. Exemplary methods, such as method 400, may be carried out in whole or in part by a wearable computer having a head-mountable display (which may further have an inward-facing camera, depending upon the particular implementation). For simplicity, a wearable computer configured as such may simply be referred to as a "head-mountable display" or "HMD" herein. Further, in an exemplary embodiment, the HMD is configured for two or more different eye-tracking processes that each can provide eye-position data.

As shown by block 402 of FIG. 4, exemplary method 400 involves the HMD carrying out at least one of two or more eye-tracking processes for which the HMD is configured, where the two or more eye-tracking processes comprise at least a first and a second eye-tracking process. At some point, the HMD determines a reliability indication for at least one of the eye-tracking processes, as shown by block 404. Then, based at least in part on the reliability indication, the HMD may determine a respective weight for each of the eye-tracking processes, as shown by block 406. The HMD may then determine combined eye position based on a weighted combination of eye-position data from the two or more eye-tracking processes, as shown by block 408. To do so, the eye-position data from each eye-tracking process may be weighted by the determined weight for the corresponding eye-tracking process.

The combined eye position may then be utilized for any purposes that eye-position data is typically used. Accordingly, method 400 may further involve the HMD using the combined eye position for one or more functions that incorporate eye-position data, as shown by block 410. As noted, some implementations may involve a computing device other than an HMD carrying out an exemplary method. Thus, block 402 may be considered to be one implementation of the more general function of instructing a computing device to utilize the combined eye position for one or more functions that incorporate eye-position data. In an implementation where another computing system, e.g., a server system, carries out an exemplary method, this function may involve the server system communicating the combined eye position to, e.g., the HMD.

In a further aspect, method 400 may be repeated in order to dynamically update the weights given to the various eye-tracking processes. For example, after carrying out blocks 402 to 510 at least once, the HMD may determine a second reliability indication for at least one of the eye-tracking processes. Thus, the HMD can re-determine the respective weight for each of the eye-tracking processes based on the second reliability indication, and then re-determine the combined eye position based on a weighted combination in which eye-position data from each eye-tracking process is weighted by the re-determined weight for the given eye-tracking process.

An exemplary embodiment may involve a number of different types of eye-tracking. For example, in method 400, the two or more eye-tracking processes may include two or more of: (a) eye-tracking based on controlled glints, (b) limbus tracking, (c) eye-tracking based on ambient glints, (d) pupil tracking, and (e) eye-tracking with inward-facing proximity sensors.

In an embodiment that incorporates limbus tracking, various limbus tracking techniques may be utilized. For example, an exemplary computing device may implement a limbus tracking process such as that described at Hammoud, *Passive Eye Monitoring*, pp. 157-168. Other limbus tracking techniques are possible as well.

More specific details of other possible eye-tracking processes are provided later in this description. In particular, exemplary eye-tracking process based on controlled glints will be described in greater detail in section IV. Further, exemplary eye-tracking process based on ambient glints will be described in greater detail in section V. It should be understood that an exemplary embodiment may additionally or alternatively incorporate other eye-tracking processes that are not described in detail herein, without departing from the scope of the invention.

A. Dynamically Switching Between Eye-Tracking Processes

In some implementations, method 400 may be periodically repeated to dynamically switch between an eye-tracking process based on ambient glints (i.e., an ambient-glint eye-tracking process) and at least one other eye-tracking process, such as eye-tracking based on ambient glints (i.e., a controlled-glint eye-tracking process) and/or a limbus-tracking process. For example, an HMD may switch between an ambient-glint eye-tracking process and another eye-tracking process such that the ambient-glint eye-tracking process is utilized when the at least one other eye-tracking process is determined to be unreliable. Other examples are also possible.

Note that in an embodiment where the HMD dynamically switches between ambient-glint eye-tracking and one or more other eye-tracking processes, block 406 may involve either (a) setting the weight for ambient-glint eye-tracking to zero (when data for one or more other processes is reliable) or (b) fully weighting ambient-glint eye-tracking and setting the weight for the other process or processes to zero (if eye-position data for the other process or processes is determined to be reliable).

In other applications, method 400 may be periodically repeated to dynamically switch between multiple eye-tracking processes based on a hierarchy of the processes. For example, consider an HMD that is capable of: (a) eye tracking based on controlled glints, (b) limbus tracking, and (c) eye tracking based on ambient glints, where the hierarchy is such that controlled-glint eye-tracking takes precedence over limbus tracking, and both controlled-glint eye-tracking and limbus tracking take precedence over ambient-glint eye-tracking. Such an HMD may periodically repeat method 400 in order to dynamically switch between the controlled-glint eye-tracking process, the limbus-tracking process, and the ambient-glint eye-tracking process.

More specifically, based on the hierarchy of eye-tracking processes, the HMD may use eye-position data from the controlled-glint eye-tracking process, so long as the controlled-glint eye-tracking process is determined to be reliable. However, when the controlled-glint eye-tracking process is determined to be unreliable, then the HMD may evaluate whether the limbus-tracking process can be considered reliable. Then, if the limbus-tracking process is determined to be reliable, the HMD may use eye-position data from the limbus-tracking process. However, if both controlled-glint eye-tracking and limbus tracking are determined to be unreliable, then the HMD may use eye-position data from the ambient-glint eye-tracking process.

B. Dynamically Weighting Multiple Eye-Tracking Processes

Note that while an HMD can implement method 400 to switch between the eye-tracking processes in a discrete manner, such as described above, an HMD may also implement method 400 in a manner such that non-zero weights for multiple eye-tracking processes are possible at block 406. In such an embodiment, the combined eye position may therefore take into account the eye-position data from all the eye-tracking processes having a non-zero weight.

In some embodiments where multiple non-zero weights are possible, a default weighting for the eye-tracking processes may specify a default weight for ambient-glint eye-tracking that is less than the weight for each of the one or more other eye-tracking process. In some cases, the default weight for ambient-glint eye-tracking may be zero. Thus, the HMD may calculate the eye position by weighting both the eye position indicated by the controlled-glint eye-tracking process and the eye position indicated by the limbus-tracking process.

In some embodiments, a Kalman filter may be applied to weight the data produced by the various eye-tracking methods and output a combined eye-tracking signal. To do so, the computing device may model of the eye and known rules of eye-movement (e.g., a maximum speed of eye movement) and eye-position estimates from two or more different eye-tracking to form an estimate of the eye's movement and/or the eye's position that hopefully is better than the estimate obtained by using a single eye-tracking process.

As an example, consider the scenario where an HMD is configured for controlled-glint eye-tracking, limbus tracking, and ambient-glints eye tracking. Both controlled-glint eye-tracking and limbus tracking may generally provide accurate eye-tracking data, but ambient light may also reduce the accuracy of both techniques. However, ambient light that obscures the limbus may not obscure the controlled glints, and vice versa. Further, the eye should be expected to move at a speed that is within the known limits of human eye movement.

To apply a Kalman filter in the above scenario, a computing device may analyze received video of the eye and estimate the eye position in a given frame using both controlled-glint eye-tracking and limbus tracking techniques. Further, the computing device may determine the covariance of the eye position determined via controlled-glint eye tracking and the eye position determined via limbus tracking. The covariance may then be used to determine the respective weights to place on controlled-glint eye-tracking and limbus tracking. A combined eye position estimate may then be determined by calculating the weighted average of the eye position determined via controlled-glint eye tracking and the eye position determined via limbus tracking. This process may be repeated for each frame in the video (or periodically, analyzing, e.g., every second, third, or fourth frame) with the newly determined eye positions and the covariance from the previous frame providing the weighting of controlled-glint eye-tracking and limbus tracking estimates of eye position.

Further, the computing system may compare the individual eye-position estimations determined via both controlled-glint eye tracking and limbus tracking to a model of the human eye. If the eye-position estimation from one of these processes does not comport with physical constraints of human eye movement, then the computing device may rely on the other process. For example, if the angular movement that would have needed to occur in order to move from the combined eye position determined in the previous frame to the eye position indicated for the current frame by limbus tracking, would have required an eye-movement speed that was greater than physically possible, then the computing device may give limbus tracking a zero weight in the current frame, and rely solely on the eye position estimation based on limbus tracking. Furthermore, in a given frame, if the eye-position estimations from both controlled-glint eye tracking and limbus tracking do not comport with physical constraints of human eye movement, then the computing device may rely on ambient-glint eye tracking to determine the eye position for the frame.

C. Exemplary Reliability Indications

As noted, block 404 of method 400 involves determining a reliability indication for at least one eye-tracking process. Various types of reliability indications are possible. Further, various techniques may be used to determine a given type of reliability indication.

As one specific example, consider a scenario where an HMD is configured for eye-tracking based on ambient glints and eye-tracking based on controlled glints. Further, controlled-glint eye-tracking may involve the HMD analyzing a video of the eye to detect controlled glints, determining a spatial relationship between the controlled glints that are detected in the video, and then determining an eye position based on the spatial relationship. Further, limbus-tracking may involve analyzing the video of the eye to detect at least a portion of limbus, determining the shape and/or location of the limbus as captured in the video, and then determining an eye position that corresponds to the detected shape and/or location of the limbus. Yet further, ambient-glint eye-tracking may involve the HMD analyzing the video of the eye to detect ambient glints (e.g., reflected features), and then determining an eye position based on the ambient glints that are detected.

In this scenario, block 404 may involve determining that the features upon which one or more of the eye-tracking methods are based cannot be detected in the video (or that what is detected is not reliable enough). For example, when the HMD analyzes the video of the eye in an effort to detect controlled glints, the HMD may be unable to detect the controlled glints or, if controlled glints are detected, may determine that the controlled glints are not suitable for the controlled-glints eye-tracking process. In this case, the HMD may respond by increasing the weight given to limbus tracking and/or increasing the weight given to ambient-glint eye-tracking (and reducing the weight given to controlled-glint eye-tracking).

As another example, when the HMD analyzes the video of the eye in an effort to detect at least a portion of the limbus, the HMD may determine that the video does not capture the limbus, or at least a portion of the limbus that is suitable for the limbus-tracking process. In this case, the HMD may respond by increasing the weight given to controlled-glint eye-tracking and/or increasing the weight given to ambient-glint eye-tracking (and reducing the weight given to limbus tracking).

As yet another example, the covariance determined when implementing a Kalman filter, as described above, may be considered to be type a reliability indication. Other types of reliability indications and/or combinations of reliability indications are possible as well.

IV. Eye-Tracking Based on Controlled Glints

Some eye-tracking techniques utilize "controlled glints" to determine eye movements. In particular, a number of light sources may be directed at the eye such that the reflections of these light sources in the eye (i.e., the controlled glints) may be recorded by a video camera that is also directed at the eye. The controlled glints may then be analyzed to determine the general position of the eye.

As a specific example, four light sources may be configured to provide a square or rectangular arrangement of glints on the eye. However, due to the shape of the eye, the generally square arrangement of glints will be warped according to the position of the eye. Accordingly, the manner in which the arrangement of glints warps from frame to frame may be analyzed to determine how the eye has moved between frames.

More specifically, to determine eye movement from controlled glints, frames of the video image may be flattened. The flattening process maps the ellipsoid shape of the corneal surface of the eye to a two-dimensional image, such that the actual distance between glints on the corneal surface is represented in the two-dimensional image. An exemplary system may then determine optical flow between the flattened frames, which is indicative of how the glints moved between frames. The optical flow may then be re-mapped to the corneal surface in order to determine how the eye has moved.

While the above example may be an efficient technique for eye-tracking in some scenarios, ambient light can often interfere with controlled glints. More specifically, ambient light may also reflect of the eye and create "ambient glints," which may also be captured by the video of the eye. In some instances, the ambient-light reflections may make it difficult or even impossible to determine whether a glint is a controlled glint or an ambient glint. Thus, ambient light can make eye-tracking data based on controlled glints inaccurate.

In order to help distinguish controlled glints from ambient glints, an exemplary embodiment may switch off one light source in each frame, and rotate the light source that is switched off. For example, consider the above example with four light sources configured to provide a generally square arrangement of controlled glints. In this configuration, an exemplary system may switch off one light source during each frame of the video, rotating the switched-off light source such that each light source is switched off every fourth frame. As such, the general structure of the controlled glints will be known in each frame, which may help to distinguish the controlled glints from ambient glints.

In a further aspect of an exemplary embodiment, the light sources and the video camera to capture the glints may be implemented on a wearable computer with a head-mounted display (HMD). In particular, the lens frame of a glasses-style HMD may include an array of inward-facing light sources (e.g., LEDs) and an inward-facing video camera, which are both directed at the eye.

A. Exemplary HMD-Implemented Methods

Figure 5:
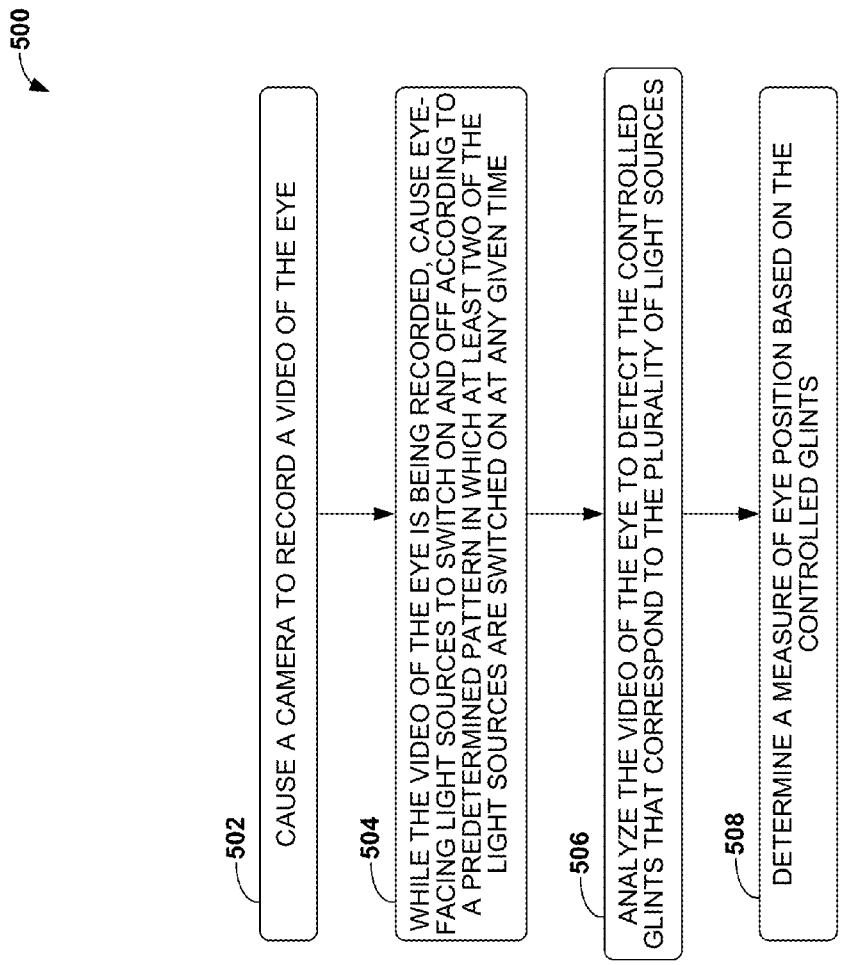
FIG. 5 is a flow chart illustrating a method, according to an exemplary embodiment.

FIG. 5 is a flow chart illustrating a method 500, according to an exemplary embodiment. Exemplary methods, such as method 500, may be carried out in whole or in part by a wearable computer having a head-mountable display (which may further have an inward-facing camera, depending upon the particular implementation). For simplicity, a wearable computer configured as such may simply be referred to as a "head-mountable display" or "HMD" herein.

As shown by block 502 of FIG. 5, exemplary method 500 involves an HMD causing a camera that is attached to the HMD to record a video of the eye. While the video of the eye is being recorded, the HMD causes a number (e.g., three or more) of eye-facing light sources, which may be attached to the HMD, to switch on and off according to a predetermined pattern in which at least two of the light sources are switched on at any given time while the video of the eye is being recorded, as shown by block 504. The HMD may then analyze the video of the eye to detect the controlled glints that correspond to the plurality of light sources, as shown by block 506. Then, the HMD may determine a measure of eye position based on the controlled glints, as shown by block 508.

i. Switching Light Sources On and Off According to a Predetermined Pattern

As noted above, at block 504, the light sources are switched on and off according to a predetermined pattern in which at least two light sources are switched on at any given point in time. As a general example, such a predetermined pattern may involve switching off just one of the light sources at a given time and changing the switched-off light source one or more times while the video of the eye is being recorded, according to a predefined schedule. Other general examples are also possible.

In some embodiments, the predetermined pattern may be a predetermined sequence of light-source combinations, with each combination having certain light sources that are turned on. Further, in such an embodiment, the sequence of light-source combinations may be repeated.

Figure 6A:
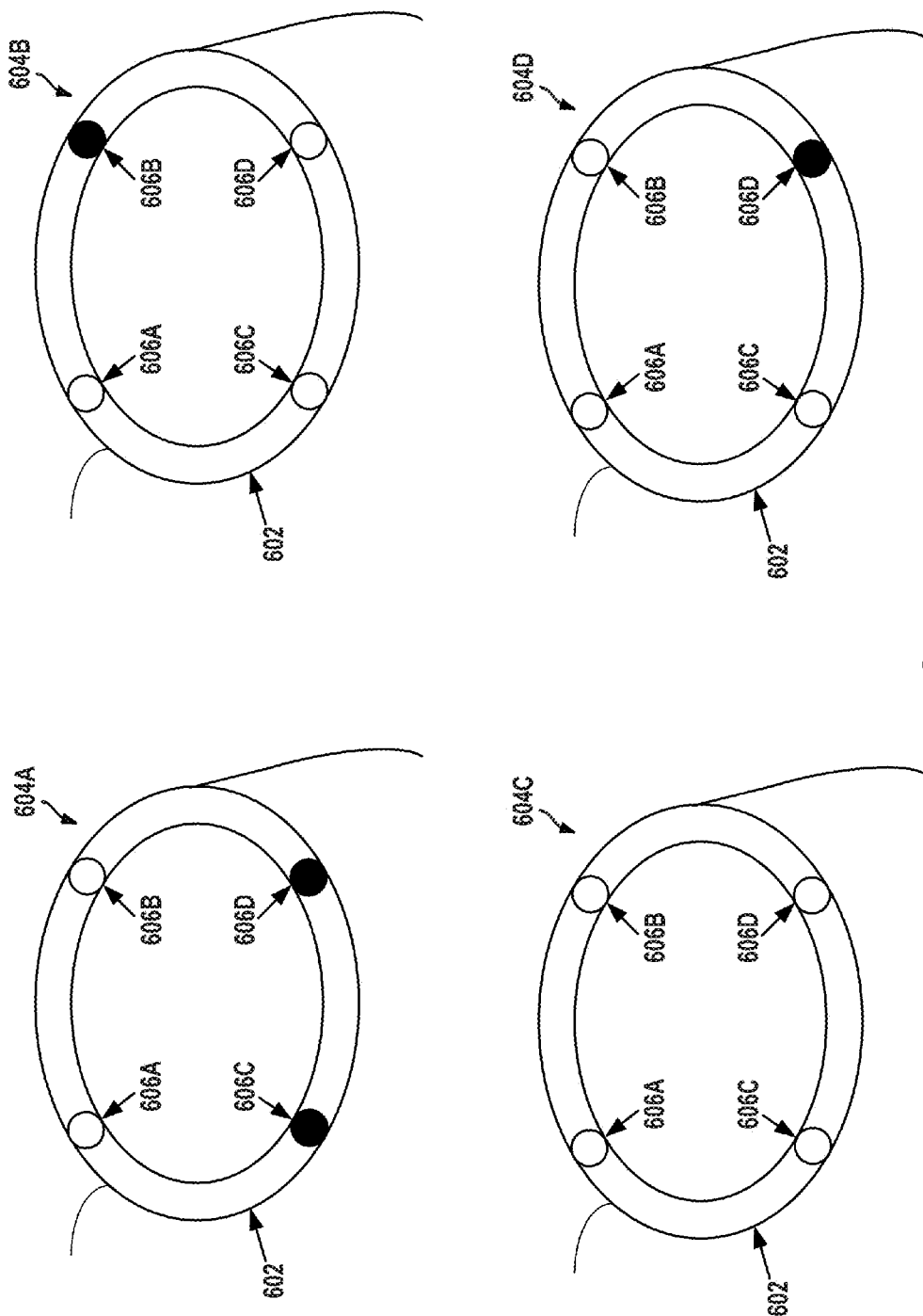
FIG. 6A is a simplified illustration of a predetermined sequence of light-source combinations, according to an exemplary embodiment.

FIG. 6A is a simplified illustration of a predetermined sequence of light-source combinations, according to an exemplary embodiment. Specifically, FIG. 6A shows an HMD 602 going through a sequence of four light-source combinations 604A to 604D. To do so, HMD 602 includes four light sources 606A to 606D, which are attached to the frame of HMD 602 and have a substantially rectangular spatial relationship with one another. Configured as such, HMD 602 may individually switch light sources 606A to 606D on and off according to a predetermined pattern. (Note that for purposes of illustration in FIG. 6A, switched-off light sources are black and switched-on light sources are white.)

In the illustrated embodiment, the predetermined pattern may be the sequence of light-source combinations 604A to 604D. As such, the HMD 602 may initially turn on light sources 606A and 606B in order to form light-source combination 604A. Then, after a predetermined period of time, the HMD may turn on light sources 606A, 606C, and 606D to form light-source combination 604B. After again waiting the predetermined period of time, the HMD 602 may turn on all the light sources 606A to 606D to form light-source combination 604C. Next, and again after waiting the predetermined period of time, HMD 602 may turn on light sources 606A to 606C to form light-source combination 604D. Further, the HMD 602 may repeat the above cycle of light-source combinations 604A to 604D one or more times.

ii. Analyzing the Video to Detect Controlled Glints

Since the timing of the sequence of light-source combinations is generally known, an HMD may know which glints to search when analyzing the video of the eye to detect controlled glints. More specifically, at block 506 of method 500, the HMD may analyze individual frames of the video for controlled glints captured in each frame. To do so, the HMD may first determine which light sources were switched on when the frame was recorded (e.g., by determining what combination in the sequence was formed when the frame was recorded). As such, the HMD can more efficiently analyze the frame by searching for just the controlled glints that correspond to the light sources that were switched on when the frame was recorded.

Figure 6B:
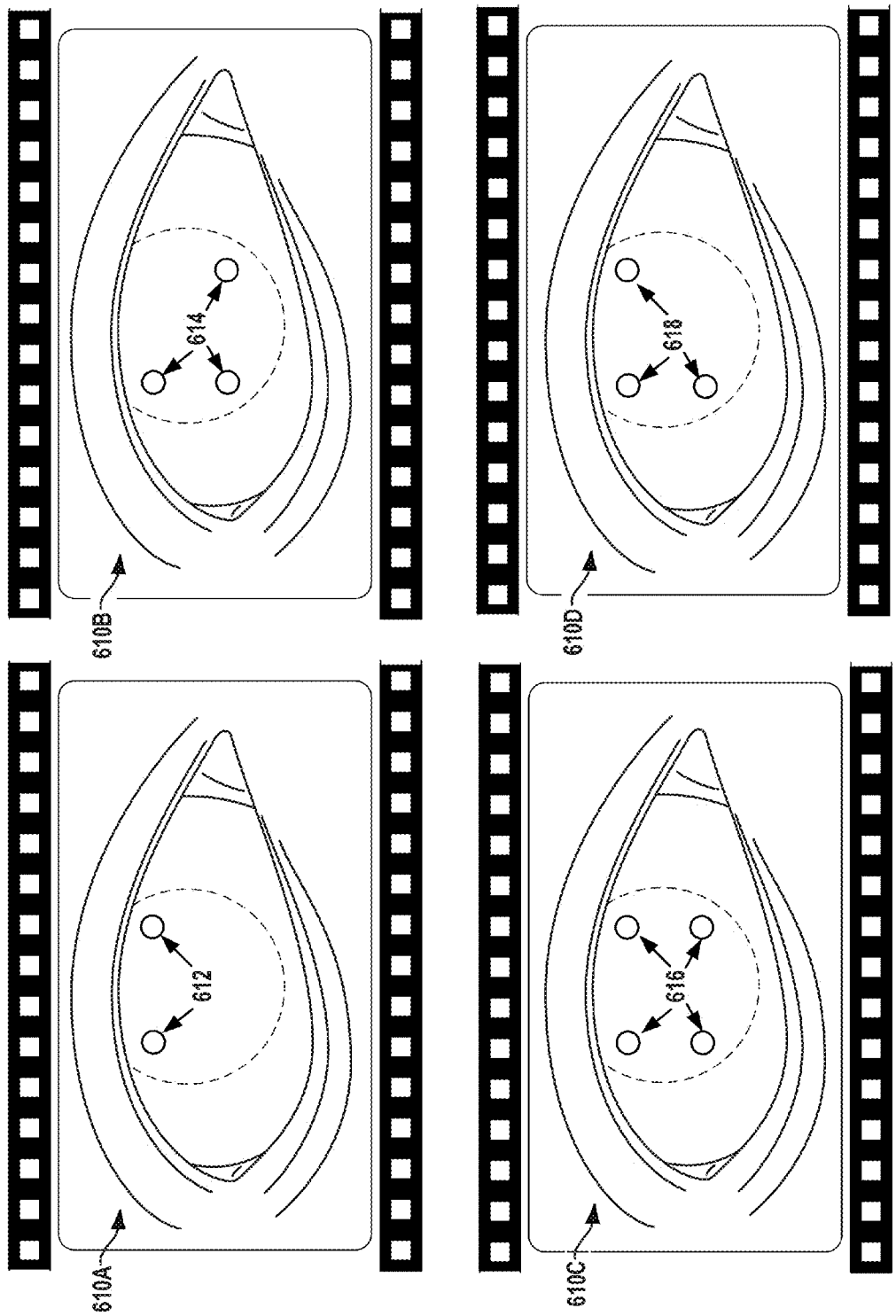
FIG. 6B is a simplified illustration of frames from a video of the eye that is captured during the sequence of light-source combinations shown in FIG. 6A, according to an exemplary embodiment.

FIG. 6B is a simplified illustration of frames from a video of the eye that is captured during the sequence of light-source combinations shown in FIG. 6A, according to an exemplary embodiment. In particular, frames 610A to 610D capture controlled the glints that correspond to light-source combinations 604A to 604D, respectively.

More specifically, frame 610A captures controlled glints 612 that correspond to light-source combination 604A (i.e., controlled glints that result from light sources 606A and 606B reflecting off the eye). Similarly, frame 610B captures controlled glints 614 that correspond to light-source combination 604B (i.e., controlled glints corresponding light sources 606A, 606C, and 606D), frame 610C captures controlled glints 616 that correspond to light-source combination 604C (i.e., controlled glints corresponding all light sources 606A to 606D), and frame 610D captures controlled glints 618 that correspond to light-source combination 604D (i.e., controlled glints corresponding light sources 606A to 606C).

Note that in some embodiments, light-sources forming one light-source combination in a sequence may be left on until it is time for the next light-source combination in the sequence. In such an embodiment, a light source that is switched on in consecutive light-source combinations in the predetermined sequence may simply be left on when the HMD switches from the first of the consecutive combinations to the second. For example, in such an embodiment, switching from light-source combination 604A to light-source combination 604B may involve switching off light source 606B, switching on light sources 606C and 606D, and simply leaving light source 606A switched on. Other examples are also possible.

In other embodiments, an HMD may turn off all light sources in between light-source combinations in the sequence. For example, the HMD may turn on the light sources for a given combination for a certain period of time and then turn off all the light sources for a certain period of time before turning on the light source that form the next combination in the sequence.

Note that the period for which each combination is formed and/or the period for which the HMD turns off all light sources between combinations in the sequence may vary, depending upon the particular implementation. For instance, in some implementations, the HMD 602 may flash light-source combinations such that each light-source combination is formed for a short period, with the light sources otherwise being turned off. By turning off the light sources in between combinations in the sequence, such an implementation may help to conserve power and/or may provide other benefits.

Further, in such an implementation, the timing with which the HMD flashes the light-source combinations may be substantially phase-synchronized with the frames of the video that is capturing the eye. For example, the light-source combinations may be flashed such that glints corresponding to the switched-on light sources are captured in each video frame. To do so, the sequence of light-source combinations may be timed according to the frame rate of the video, such that the HMD forms the next combination in the sequence before the next frame in the video of the eye is captured. Thus, for any two consecutive frames in the video of the eye, the light-source combination that is formed when the first of two consecutive frames is recorded will differ from the light-source combination that is formed when the second of the consecutive frames is recorded.

In some embodiments, the predetermined pattern with which the light sources are switched on and off may be such that no more than one light source is switched off in any given light-source combination. Since having more light sources generally results in having more controlled glints that can be used to determine eye position, increasing the number of switched on light sources when a given image of the eye is captured may improve the accuracy with which eye position can be measured based on the corresponding glints. Thus, a sequence of light-source combinations in which no more than one light source is switched off in any given combination, may facilitate more accurate eye tracking than a sequence that includes combinations with more than one light source switched off.

FIG. 7 is a simplified illustration of a predetermined sequence of light-source combinations, according to an exemplary embodiment. Specifically, FIG. 7 illustrates a sequence of light-source combinations 704A to 704D in which no more than one light source is switched off in any given combination. More specifically, in the first light-source combination 704A in the sequence, light source 706A is switched off, while light sources 706B, 706C, and 706D are switched on. In the second light-source combination 704B in the sequence, light source 706B is switched off, while light sources 706A, 706C, and 706D are switched on. In the third light-source combination 704C in the sequence, light source 706C is switched off, while light sources 706A, 706B, and 706D are switched on. Lastly, in the fourth light-source combination 704D in the sequence, light source 706D is switched off, while light sources 706A, 706B, and 706C are switched on.

It should be understood that the examples in FIGS. 6A, 6B, and 7 are provided for illustrative purposes, and that numerous variations on the illustrated examples and other examples are possible. For instance, while FIGS. 6A, 6B, and 7 illustrate an HMD with four light sources arranged in a rectangular relationship, the number of light sources and arrangement of light sources on the HMD may vary. Further, while FIGS. 6A, 6B, and 7 illustrate examples in which the predetermined pattern takes the form of a sequence of four light-source combinations, the number of light source combinations in such a sequence may vary, without departing from the scope of the invention. Other examples and variations on the above described examples are possible as well.

iii. Determining Eye Position Based on Controlled Glints

Referring back to blocks 506 and 508 FIG. 5, an HMD may use various techniques to determine a measure of eye position based on the detected glints. In particular, the HMD may determine an eye position on a frame by frame basis. Thus, as each frame is evaluated, the HMD may determine the eye position at the time the frame was recorded.

For example, at block 506 of method 500, the HMD may have determined which light sources were switched on when a given frame was recorded (e.g., the light-source combination corresponding to the frame) and, if analysis of the frame is successful, will have detected controlled glints that correspond to the particular light-source combination. As such, to determine eye position at block 508, the HMD may determine the spatial relationship between the controlled glints that are detected in a given frame, and then determine an eye position based on this spatial relationship.

In particular, the spatial relationship between controlled glints in a frame may vary depending upon the position of the eye. More specifically, since the light sources are generally fixed, but the curvature of the surface of the eye is such that the distance from the surface of the eye to a fixed light source will typically vary as the eye rotates within the orbit. Thus, the angle at which the light source reflects from the surface of the eye (e.g., from the cornea and/or sclera) may vary depending upon the position of the eye. Therefore, when multiple fixed light sources are directed towards the eye, the spatial relationship between the glints corresponding to the light sources may vary, depending upon the respective angles of reflection that result from the current eye position. More details of such a method (albeit without any variation in which light sources are switched on and off) are described in Hammoud, Passive Eye Monitoring, pp. 136-141, 202-204.

In a further aspect, by determining the eye position over the course of a video with multiple frames, the HMD may evaluate eye movement during the time when the video was recorded. For example, to determine eye movement, the HMD may determine the change in eye position over the two or more frames of the video. The HMD may then quantify the change in position by, e.g., determining an eye-movement value (e.g., an angular movement of the eye in the orbit) that corresponds to the change in eye position over the two or more frames of the video. Other examples are also possible.

It should be understood that while exemplary methods such as method 500 are described by way of example as being implemented by an HMD, an exemplary method may also be implemented in whole or in part by other types of computing devices. For example, an exemplary method may be implemented in whole or in part by a mobile phone, a tablet computer, a laptop or desktop computer equipped with a camera, and/or a network-enabled camera. Other examples of computing devices or combinations of computing devices that can implement an exemplary method are possible. In general, an exemplary method may be implemented by any computing device, system, or combinations of computing device(s) and/or system(s) that are configured to provide the same or similar functions as described herein.

B. Exemplary Cloud-Based Methods

As noted above, an exemplary method may also be carried out in whole or in part by a device or system, or by a combination of one or more devices and/or one or more systems, which are in communication with and can receive eye-tracking data from a device or system that captures the eye tracking data (e.g., an HMD). For example, an exemplary method may be implemented in whole or in part by a server system, which receives data from a device such as an HMD.

Figure 8:
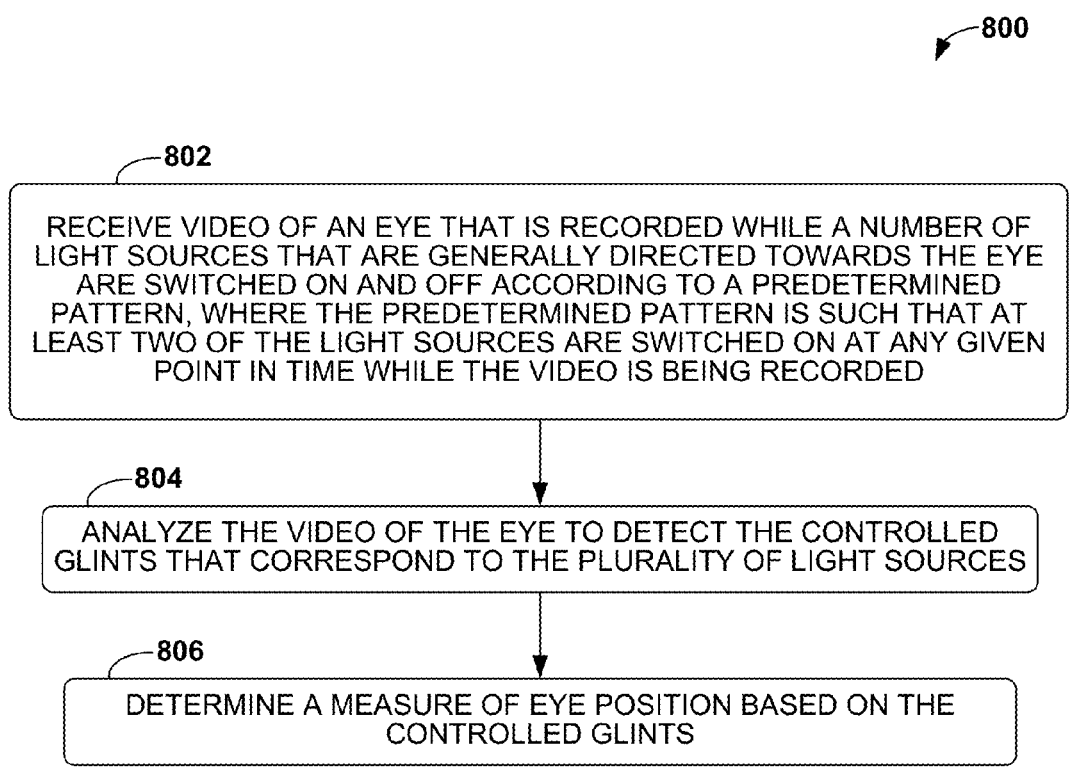
FIG. 8 is a flow chart illustrating a method that may be carried out by a server system, according to an exemplary embodiment.

FIG. 8 is a flow chart illustrating a method that may be carried out by a server system, according to an exemplary embodiment. It should be understood that while method 800 is described by way of example as being carried out by a server system (e.g., a cloud-based server), other device(s) and/or system(s) may carry out a method such as method 800, without departing from the scope of the invention.

As illustrated by block 802, an exemplary method 800 may involve a server system receiving video of an eye that is recorded while a number of light sources that are generally directed towards the eye are switched on and off according to a predetermined pattern, where the predetermined pattern is such that at least two of the light sources are switched on at any given point in time while the video is being recorded. The server system then analyzes the video of the eye to detect controlled glints that correspond to the plurality of light sources, as shown by block 804. The server system then determines a measure of eye position based on the controlled glints, as shown by block 806.

It should be understood that the above eye-tracking processes based on controlled glints are provided for purposes of illustration and are not intended to be limiting. Other eye-tracking processes and/or variations on the above-described processes are also possible.

V. Eye-Tracking Based on Ambient Glints

As noted above, an exemplary HMD may include an inward-facing camera or cameras that are configured to capture images of the wearer's eye or eyes. The images of the wearer's eye may be video and/or still images, depending upon the particular implementation. Further, the cornea and/or the sclera may reflect light from the wearer's eye. Such reflections may therefore be captured in images of the wearer's eye. Since the eye typically reflects an image of what the wearer is viewing, reflections captured in images of the eye may be indicative of what the wearer is looking at.

Typically, when an HMD is worn, the image reflected from the wearer's eye (referred to herein as a "reflected image" or simply a "reflection") may change as the eye moves in space. In particular, due to the shape of the eye, reflected features may warp and or move on the surface of the eye as the eye moves. Such changes to the reflected image may generally be referred to as "movement" of the reflected image. As such, the movement of a reflected image between two images can be used to determine how much the eye moved in space. However, the movement of the eye in space occurs when the head moves and when the eye itself moves (e.g., when the eyeball moves in the orbit). Therefore, when there is movement in a reflected image, it may not be readily apparent how much of the movement is due to head movement, and how much results from orbital movement of the eye itself.

Accordingly, exemplary embodiments may help to determine the head-movement component and/or the orbital component that make up the overall movement of the eye in space, based on a corresponding movement of the image reflected from the eye. To do so, an HMD may implement an expectation maximization process where it alternatingly estimates the head-movement component and the orbital component of an observed eye movement until the combination of the estimated head-movement component and the estimated orbital component match, or are acceptably close to, the observed movement of the eye in space.

More specifically, the HMD may use head-movement data provided by accelerometers and/or gyroscopes on the HMD, for example, to determine how the head moved during a given period of time and, correspondingly, how the eye moves in space as a result of this head-movement. This serves as the estimate of the head-movement component of the overall eye movement. Accordingly, the HMD may then calculate how the image reflected from the eye is expected to move based on only the head-movement component of the eye movement, and compare the expected movement to the movement of the reflected image that is actually observed during the period. The difference between the expected and observed movement, if any, may be attributed to the orbital component of the eye movement. As such, the HMD may use the difference in movement to estimate the orbital component of eye movement.

The HMD may then combine the head-movement component and the orbital component to determine an expected overall eye movement, assuming these estimations are correct. The HMD may then test the estimated components by comparing the expected movement of the reflected image, which would occur if the expected eye movement were correct, to the observed movement of the reflected image.

If the difference between the expected and observed movement of the reflected image is deemed significant, then the HMD may adjust assumptions and/or parameters and recursively repeat the process until the difference is less than a threshold. When the difference between the expected movement and the observed movement is less than the threshold, then the HMD may set eye movement data to be the period being evaluated based on the current estimate of the orbital component and/or the current estimate of the head-movement component.

In some cases, the difference between the expected and observed movement may be attributable to inaccurate data from the gyroscope and/or accelerometer. Accordingly, the wearable computer may adjust how data from the gyroscope and/or accelerometer is interpreted. Further, due to variations between wearers, the model of the human body that is applied when determining the amount of eye movement that is attributable to head movement, may also be inaccurate. Similarly, assumptions as to the location of the eye with respect to the gyroscope and/or accelerometer may also lead to inaccuracies. Thus, the wearable computer may additionally or alternatively adjust its model of the human body (e.g., with respect to the head, neck, and/or eye), and/or may adjust its assumption with regards to the location of the eye relative to the sensors in the HMD. In accordance with typical expectation maximization procedure, the adjustments may be gradual.

Note that in an exemplary embodiment, a reflected image may include reflections of various features in a person's environment. The individual features within a reflected image may each be referred to as a "reflected feature." For example, a reflected feature may be a "glint" that results from a light source that reflects from the wearer's eye. A reflected feature may also be defined by an absence of light that occurs when a source (e.g., a person or object) blocks a light source and wholly or partially prevents the light sources from reflecting from the eye. Reflected features may take other forms as well.

Figure 9:
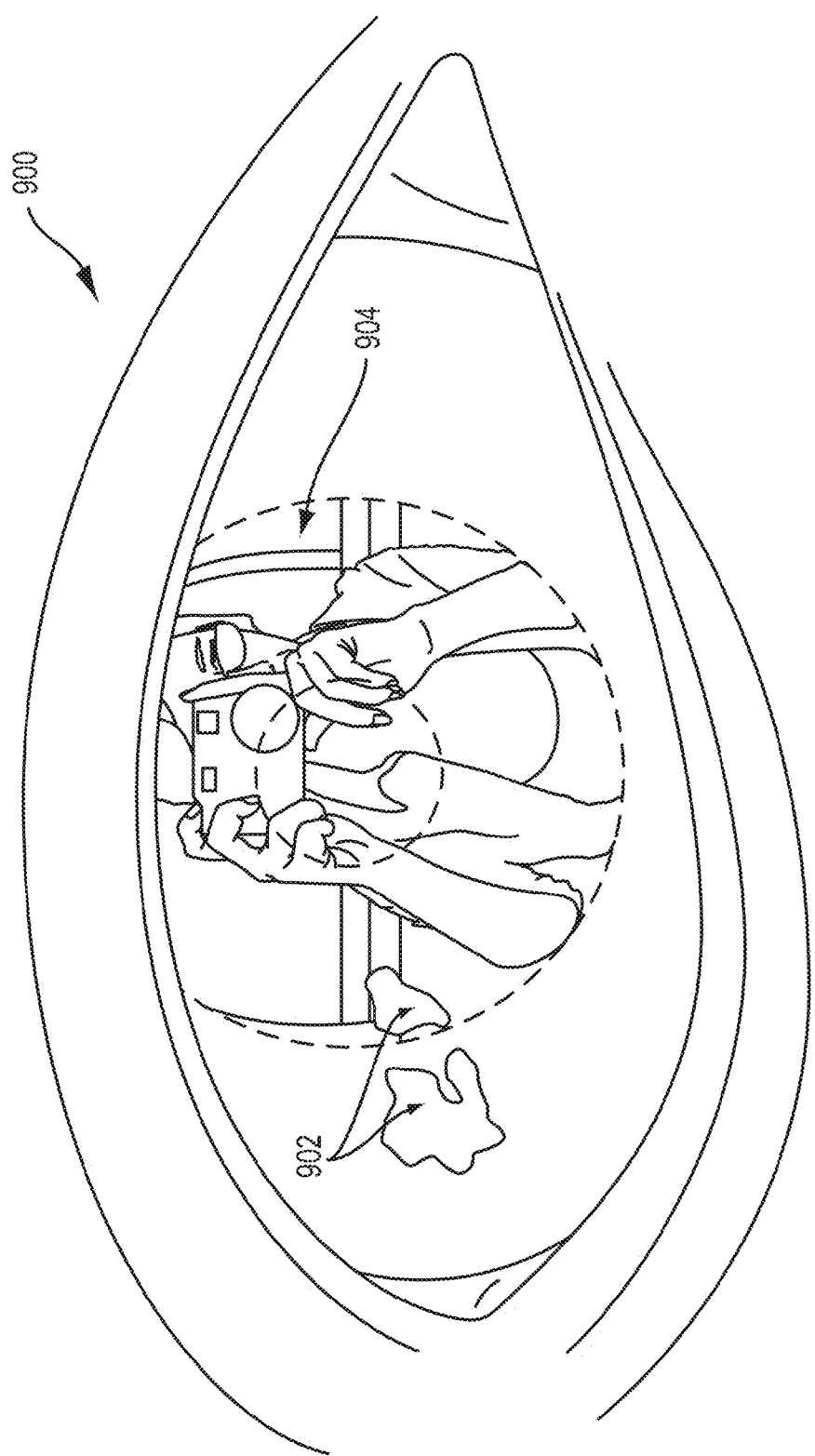
FIG. 9 illustrates reflected features that may be captured in an image of the eye, according to an exemplary embodiment.

FIG. 9 illustrates reflected features that may be captured in an image of the eye, according to an exemplary embodiment. In particular, the illustrated image of the eye 900 includes reflected features 902 and 904. Reflected features 902 are glints, which result from a light source reflecting from the surface of the eye 900. Reflected feature 904, on the other hand, is a darker feature that results from its source blocking a light source. Specifically, in the illustrated example, the source of reflected feature 904 is a person who is capturing the image of eye 900. It should be understood that herein, a "reflected image" may be an image of the entire eye, an image of an entire portion of the eye image (e.g., the corneal surface), or may be a set of one or more reflected features that collectively define the reflected image.

Figure 10:
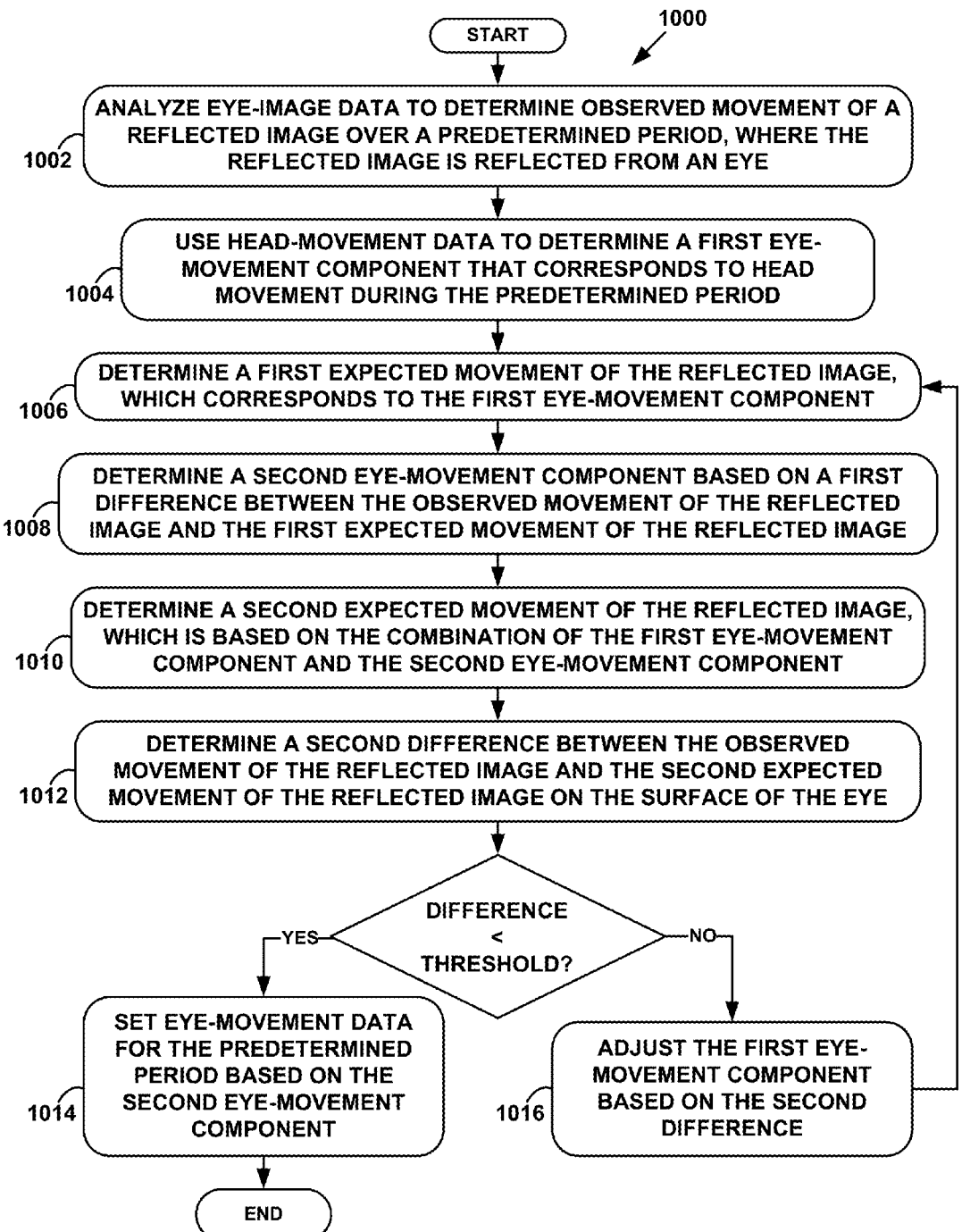
FIG. 10 is a flow chart illustrating a method, according to an exemplary embodiment.

FIG. 10 is a flow chart illustrating a method 1000, according to an exemplary embodiment. Exemplary methods, such as method 1000, may be carried out in whole or in part by a wearable computer having a head-mountable display (which may further have an inward-facing camera, depending upon the particular implementation). For simplicity, a wearable computer configured as such may simply be referred to as a "head-mountable display" or "HMD" herein.

Accordingly, exemplary methods may be described by way of example herein as being implemented by an HMD. However, it should be understood that an exemplary method may be implemented in whole or in part by other types of computing devices. For example, an exemplary method may be implemented in whole or in part by a server system, which receives data from a device such as an HMD. As further examples, an exemplary method may be implemented in whole or in part by a mobile phone, tablet computer, or laptop computer equipped with a camera, by a network-enabled camera, and/or by other computing devices configured to capture and/or receive eye-image data. Other examples of computing devices or combinations of computing devices that can implement an exemplary method are possible.

As shown by block 1002 of FIG. 10, exemplary method 1000 involves an HMD analyzing eye-image data to determine observed movement of a reflected image over a predetermined period, where the reflected image is reflected from an eye, as shown by block 1002. The HMD may then use head-movement data to determine a first eye-movement component that corresponds to head movement during the predetermined period, as shown by block 1004. The HMD may then determine a first expected movement of the reflected image, which corresponds to the first eye-movement component, as shown by block 1006. The HMD may also determine a second eye-movement component based on a first difference between the observed movement of the reflected image and the first expected movement of the reflected image, as shown by block 1008.

Further, the HMD may determine a second expected movement of the reflected image, which is based on the combination of the first eye-movement component and the second eye-movement component, as shown by block 1010. The HMD may then determine a second difference between the observed movement of the reflected image and the second expected movement of the reflected image on the surface of the eye, as shown by block 1012. If the second difference is less than a threshold difference, then the HMD may set eye-movement data for the predetermined period based on the second eye-movement component, as shown by block 1014. On the other hand, if the second difference is greater than the threshold difference, then the HMD adjusts the first eye-movement component based on the second difference, as shown by block 1016. The HMD may then repeat blocks 1006 to 1016 recursively until the difference determined at block 1012 is less than the threshold, at which point the HMD sets eye-movement data for the predetermined period based on the second eye-movement component, as shown by block 1014.

A. Eye-Image Data

In an exemplary embodiment, the eye-image data may take various forms, and may be captured by and/or received from various devices. In some implementations, eye-image data may take the form of two or more still photographs of an eye (or a portion of the eye, such as the cornea or the iris). In other implementations, eye-image data may take the form of video of an eye. In such an implementation, two or more frames from the video may be analyzed to determine eye movement during the two frames.

Further, images of the eye (e.g., either still images or frames from a video) may be processed so as to isolate the cornea. In this case, the eye-image data may be two or more images of the surface of the cornea, and thus may provide the corneal field-of-view (FOV) at the time when each such image is captured. Other forms of eye-image data are also possible.

B. Reflected Images

As noted above, a reflected image may take various forms. For instance, as further noted above, a reflected image may be defined be a set of one or more reflected features within an image of the eye. For example, as illustrated by reflected features 902 of FIG. 9, a reflected feature may be a glint. Herein, a glint should generally be understood to be reflected light from the surface of the eye (e.g., a reflection off the cornea and/or sclera). Additionally, a reflected feature may be a reflection from a single light source or a reflection that combines light from two or more light sources.

Further, various types of glints exist. For example, a glint may be "controlled," which means that the glint is a reflection of light from a light source that is located at a known location. However, a glint may also be "uncontrolled" or "ambient," which means that the glint is a reflection of light from a light source at an unknown location. (Note that the terms "uncontrolled glint" and "ambient glint" are used interchangeably herein.)

Reflected features 902 in FIG. 9 are examples of ambient glints, for which the distance to the source is unknown. Note that any reflection from a light source at an unknown location may be considered an ambient glint, even if the light source itself is not an ambient light source (i.e., a light source outputting light that effects everything in the person's environment equally). As such, an ambient glint may in fact be a reflection of a point light source such as a street light, a desk lamp, or a nearby computer screen, among others.

Note that because the source of a controlled glint is known, it may be an unnecessary exercise to perform an exemplary method to determine the z-distance to the source of a controlled glint. However, this should not be interpreted to limit an exemplary method to implementations involving uncontrolled or ambient glints. In many implementations, an exemplary method may be applied equally for controlled and uncontrolled glints.

As further noted above, a reflected feature may also be a darker feature that is defined by edges where the feature blocks out glints, such as reflected feature 904 shown in FIG. 9. Such a reflected feature may be defined by a number of glints, each of which has a portion blocked out by the source object. Alternatively, such a reflected feature may result from a source object blocking out a portion of a single light source.

More generally, a reflected feature may be any aspect of a person's environment that is discernible from an image capturing reflections from the person's eye. Such a reflected feature may be identified by, for example, detecting the contrast at the edge between the feature and other reflected areas or features in the image of the eye, or by using other techniques.

C. Head-Movement Data

In an exemplary embodiment, head-movement data may be received from one or more sensors of an HMD. For example, a typical HMD might include one or more accelerometers and one or more gyroscopes. Other sensors are possible as well. For instance, sensors could also include a camera, a shock sensor, an impact sensor, a contact sensor (e.g., capacitive sensing device), a location determination device (e.g., a GPS device), a magnetometer, and/or an orientation sensor (e.g., a theodolite), among others.

In a further aspect, it should be understood that head-movement data may be derived from raw data produced by sensors on an HMD (e.g., raw data from accelerometers and/or gyroscopes). In particular, raw data from motion sensors such as accelerometers and gyroscopes is indicative of how the sensors themselves are moving. Therefore, if the sensors are attached to an HMD, the data indicates how the HMD is moving. Accordingly, movement of the head may be derived by applying a model that describes the spatial relationship between the sensors on an HMD and axes of rotation for the head.

Further, while gyroscopes are generally accurate in practice, they measure velocity, not position. As such, data from a gyroscope may be integrated in order to determine the degrees of rotation about each axis. Therefore, to quantify the movements of a gyroscope in 3D space, an HMD may implement various integration/estimation techniques that are well known in the art. The movement of the sensor may then be mapped to corresponding movement of the eye, and in some embodiments, to corresponding movement of the cornea in particular.

In an exemplary embodiment, head movement can typically be modeled as occurring around a pivot point in the neck. (See e.g. "The Measure of Man & Woman", Henry Dreyfuss Associates, p. 16.) Further, gyroscope(s) and/or accelerometer(s) can be mounted in a manner such that the spatial relationship of a sensor to the axes of head movement can be modeled. For example, a motion sensor could be mounted a front corner of an HMD, such that a distance to the center of rotation along the axis from the back of the head to the eyes can be modeled, and such that a distance from the center of rotation along the axis defined by the left and right eye. Further, the distances from the center of the eyeball to the center of rotation along both of the above axes may be fixed with respect to the sensor, such that the motion of the center of the eyeball can be modeled.

More specifically, since the eyeball may be modeled by an average diameter (e.g., 24 mm), this means that the cornea may be modeled as being half of the diameter (e.g., 12 mm) in front of the center of the eyeball. Given this, the motion of the corneal surface due purely to head rotation (e.g., the head-movement component of eye movement) can be calculated based on the head-movement data from the sensors.

D. Eye Movements

Sources of the reflected features that are captured in the reflected image will in most cases move in a manner that is uncorrelated to a person's head movement. Therefore, when the head moves, this typically changes the position of the eyes relative to the sources of the reflected features. As a result, movement of the image reflected from the corneal surface may occur due to both head movement and movement of the eyeball itself (e.g., movement of the eye within the orbit caused by muscular control of the eye).

Herein, movement of the eye in space that occurs as a result of head movement may be referred to as the head-movement component of eye movement. Further, movement of the eye within the orbit may be referred to herein as the orbital component of eye movement. Yet further, the movement of an eye in space due to the combination of the head-movement component and the orbital component of eye movement may be referred to herein as the total or overall eye movement.

E. Determining the Observed Movement of Reflected Image

In some embodiments, the observed movement of the reflected image may simply be indicated by an image that captures the state of the reflected image at the end of the time period for which eye movement is being determined. In such an embodiment, the observed movement may be determined by receiving, identifying, and/or processing an image reflected from the eye, which was captured at or near the end of the period.

In other embodiments, the observed movement of a reflected image may be determined by analyzing, e.g., two images of the cornea that are captured at different times. For example, movement of the reflected image on the corneal surface may be observed via a sequence of two or more corneal images. To do so, a computing system may unwarp (e.g., flatten) two or more corneal images. The computing system may then determine a feature map and/or generate a feature map of reflected features in the reflected image, which indicates the movement of the reflected image between the two corneal images.

Figure 11:
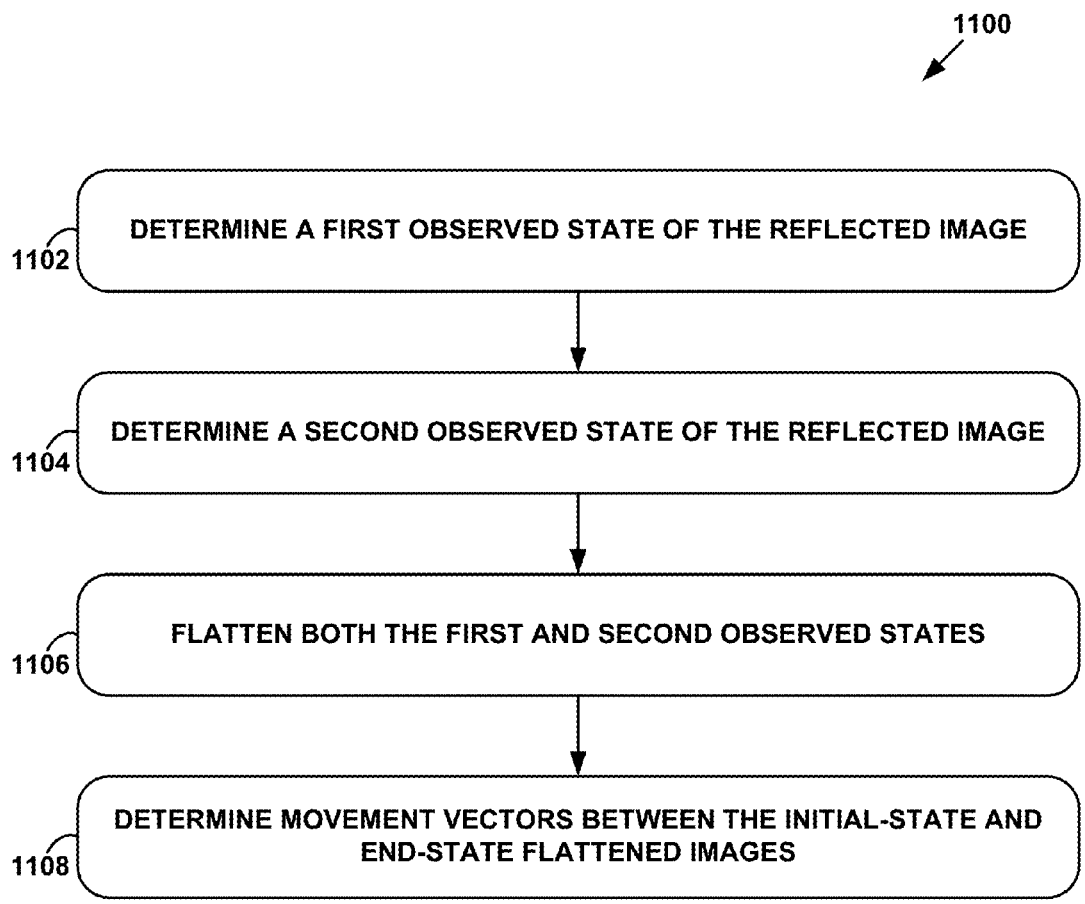
FIG. 11 is a flow chart illustrating a method for determining the observed movement of a reflected image, according to an exemplary embodiment.

FIG. 11 is a flow chart illustrating a method 1100 for determining the observed movement of a reflected image, according to an exemplary embodiment. More specifically, to determine the observed movement of the reflected image during a given period of time, an HMD may determine a first observed state of the reflected image, as shown by block 1102. The HMD may then determine a second observed state of the reflected image, as shown by block 1104. In an exemplary embodiment, the first and second observed states may be images (e.g., still images or video frames) that are captured at the beginning and end of the period for which eye movement is being determined, respectively.

Figure 12A:
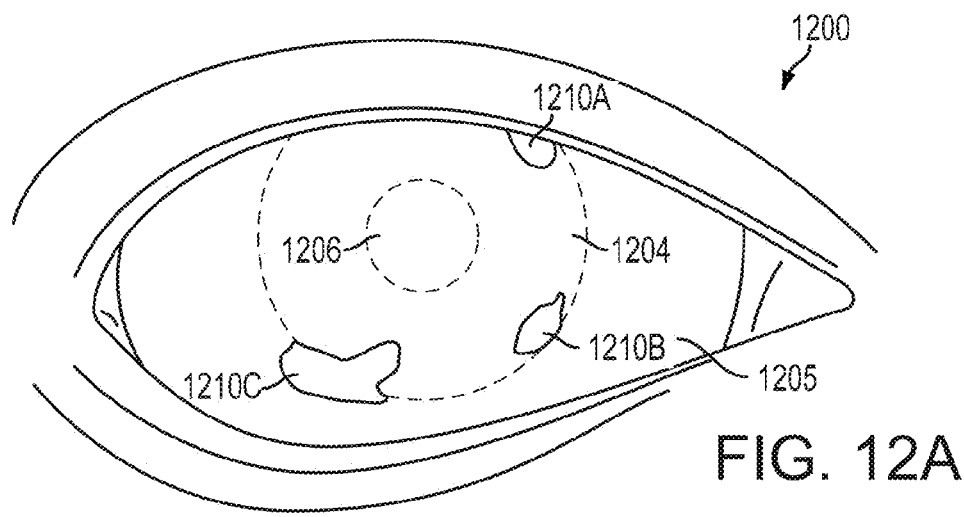
FIGS. 12A and 12B illustrate corneal images captured at the beginning and end of a time period during which eye movement is being evaluated, according to an exemplary embodiment.
Figure 12B:
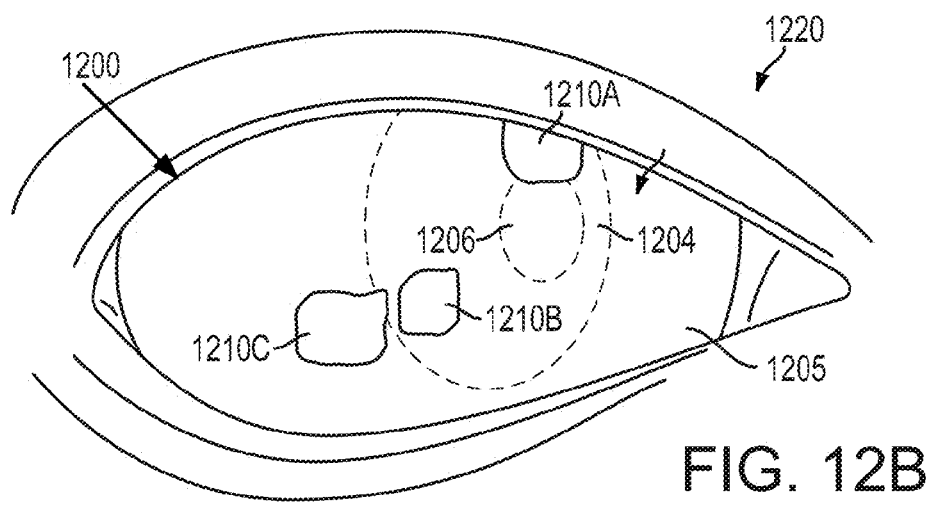

As such, the HMD may then flatten both the first and second observed states, as shown by block 1106. For example, FIGS. 12A and 12B illustrate corneal images captured at the beginning and end of a time period during which eye movement is being evaluated, according to an exemplary embodiment. The corneal images 1200 and 1220 shown in FIGS. 12A and 12B, respectively, may be captured at blocks 1102 and 1104 of the method 1100 shown in FIG. 11.

Figure 13A:
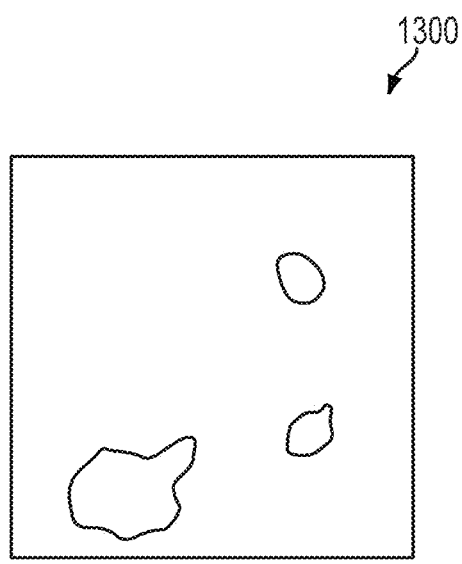
FIGS. 13A and 13B are illustrations of flattened images of the eye, according to an exemplary embodiment.
Figure 13B:
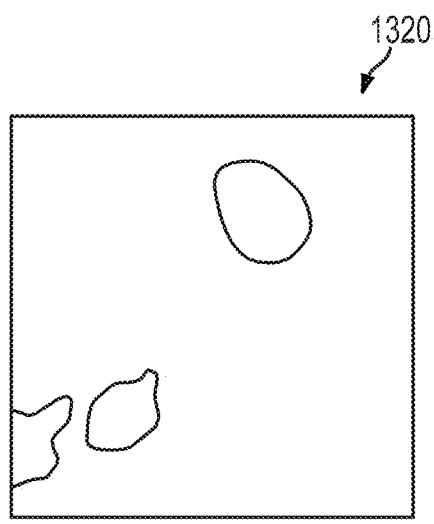

Thus, corneal images 1200 and 1220 may represent the first and the second observed states of the reflected image, respectively. For example, FIGS. 13A and 13B are illustrations of flattened images of the eye, according to an exemplary embodiment. In particular, FIG. 13A shows a flattened image 1300 that may be generated by flattening image 1200, while FIG. 13B shows a flattened image 1320 that may be generated by flattening image 1220.

Figure 14A:
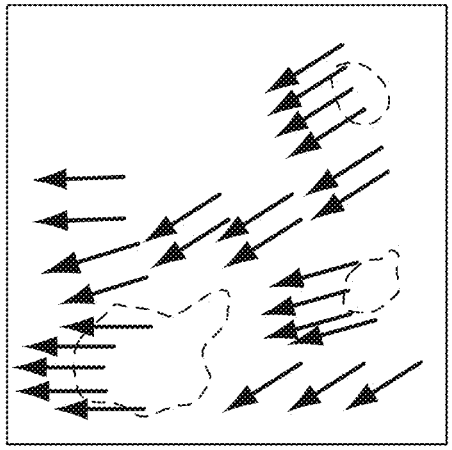
FIG. 14A is an illustration of an optical flow, according to an exemplary embodiment.

The HMD may then measure the observed movement of the reflected image by determining movement vectors between the initial-state and end-state flattened images, as shown by block 1108. To do so, once the initial observed state 1200 and the ending observed state 1220 are flattened, an HMD may generate an optical flow and/or a feature-mapping between the flattened images. More specifically, the HMD may determine the optical flow between flattened image 1300 and flattened image 1320. FIG. 14A is an illustration of an optical flow, according to an exemplary embodiment. In particular, FIG. 14A shows an optical flow 1400 between flattened image 1300 and flattened image 1320. The optical flow 1400 between the first and second state of the reflected image may thus provide a measure of the observed movement of the reflected image.

Figure 14B:
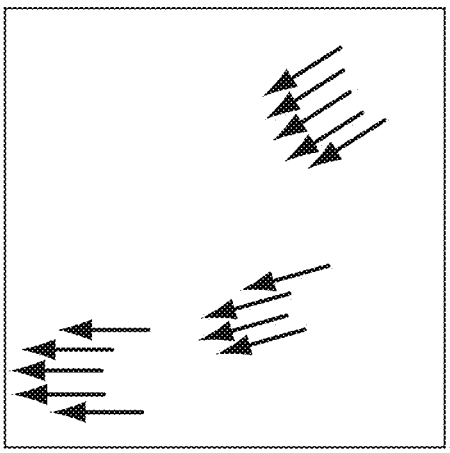
FIG. 14B is an illustration of a feature map, according to an exemplary embodiment.

Additionally or alternatively, once the optical flow 1400 between flattened image 1300 and flattened image 1320 is determined, the HMD may generate a feature map by isolating the optical flow of certain reflected features in the reflected image. For example, FIG. 14B is an illustration of a feature map, according to an exemplary embodiment. In particular, FIG. 14B shows a feature map 1402 that is based on optical flow 1400. Feature map 1402 thus includes the optical flow from the areas of reflected image 1202A where reflected features 1210A, 1210B, and 1210C are located, but has substantially removed optical flow vectors from the remaining areas of the feature map. In an exemplary embodiment, this feature map may serve as a measure of the observed movement of the reflected features 1210A, 1210B, and 1210C (and thus of the reflected image).

F. Determining an Eye-Movement Component Resulting from Head Movement

As shown in FIG. 10, at block 1004 of method 1000, the HMD may determine a first eye-movement component that corresponds to the head movement during the period for which eye movement is being determined. More specifically, in an exemplary embodiment, the first eye-movement component may be the head-movement component of the total eye movement. Accordingly, to determine the first eye-movement component, the HMD may acquire and/or process data from sensors indicating movement that correlates to head movement, such as accelerometers and gyroscopes that are attached to or included as part of an HMD. The HMD may thus derive an estimated amount of eye movement that corresponds to the amount of movement experienced by the sensors.

Further, while gyroscopes are typically accurate, they measure velocity and not position. As such, head-movement data from a gyroscope may be integrated in order to determine the degrees of rotation about each axis. Therefore, to quantify the movements of a gyroscope in 3D space, an HMD may implement various integration/estimation techniques that are well known in the art. The movement of the sensor may then be mapped to corresponding movement of the eye, and in some embodiments, to corresponding movement of the cornea in particular.

In an exemplary embodiment, head movement can typically be modeled as occurring around a pivot point in the neck. (See e.g. "The Measure of Man & Woman", Henry Dreyfuss Associates, p. 16.) Further, gyroscope(s) and/or accelerometer(s) can be mounted in a manner such that the spatial relationship of a sensor to the axes of head movement can be modeled. For example, a motion sensor could be mounted a front corner of an HMD, such that a distance to the center of rotation along the axis from the back of the head to the eyes can be modeled, and such that a distance from the center of rotation along the axis defined by the left and right eye. Further, the distances from the center of the eyeball to the center of rotation along both of the above axes may be fixed with respect to the sensor, such that the motion of the center of the eyeball can be modeled.

More specifically, since the eyeball may be modeled by an average diameter (e.g., 24 mm), this means that the cornea may be modeled as being half of the diameter (e.g., 12 mm) in front of the center of the eyeball. Given this, the motion of the corneal surface due purely to head rotation (e.g., the head-movement component of eye movement) can be calculated based on the head-movement data from the sensors.

G. Determining an Expected Movement of the Reflected Image that Corresponds to First Eye-Movement Component Once the eye movement resulting from head movement has been determined, an HMD may determine the expected movement of the reflected image. In an exemplary embodiment, the expected movement is the movement that would occur if there were no orbital component to eye movement, and all eye movement during the period resulted from head movement.

In some embodiments, the expected movement of the reflected image may be indicated by the state of the reflected image at the end of the time period for which eye movement is being determined. In such an embodiment, the expected movement may be determined by generating an image that is indicative of what the reflected image would look like after just the head-movement component of eye movement. In an exemplary embodiment, this may be accomplished extracting a portion of a spherical panorama of a person's environment that corresponds to the position the eye would be in after just the head-movement component of eye movement.

Figure 15:
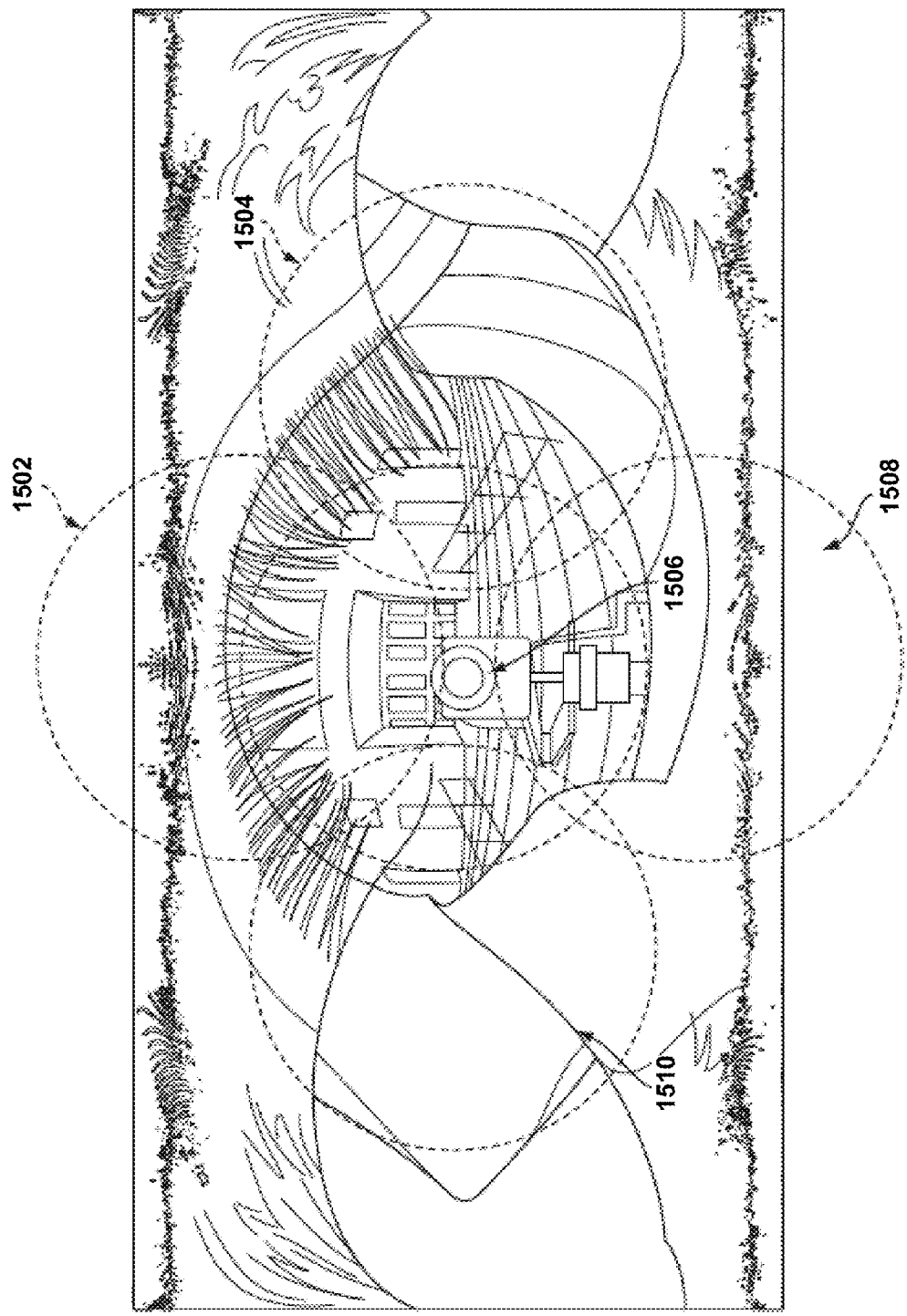
FIG. 15 is an illustration of a spherical panorama, according to an exemplary embodiment.

More specifically, FIG. 15 is an illustration of a spherical panorama 1500, according to an exemplary embodiment. In particular, spherical panorama 1500 is a multi-image spherical panorama, which may have been generated by registering and merging a number of single-image panoramas in a manner described in Nishino, K. and Nayar, S. K., "Extraction of Visual Information from Images of Eyes" in: Hammoud, R. I. (Ed.), Passive Eye Monitoring: Algorithms, Applications, and Experiments (2008 Springer-Verlag Berlin Heidelberg), pp. 170-173. Further, in the process of creating a spherical panorama, the HMD may also build a mapping of eye position to the corresponding portions the spherical panorama.

Figure 16A:
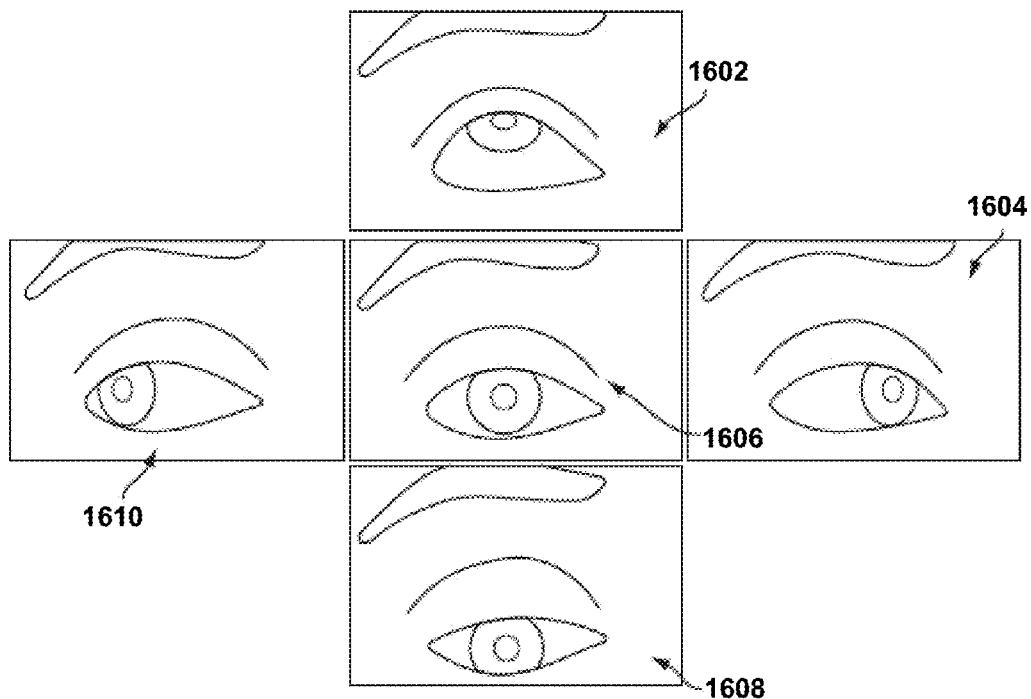
FIG. 16A is an illustration of a number of eye positions, according to an exemplary embodiment.
Figure 16B:
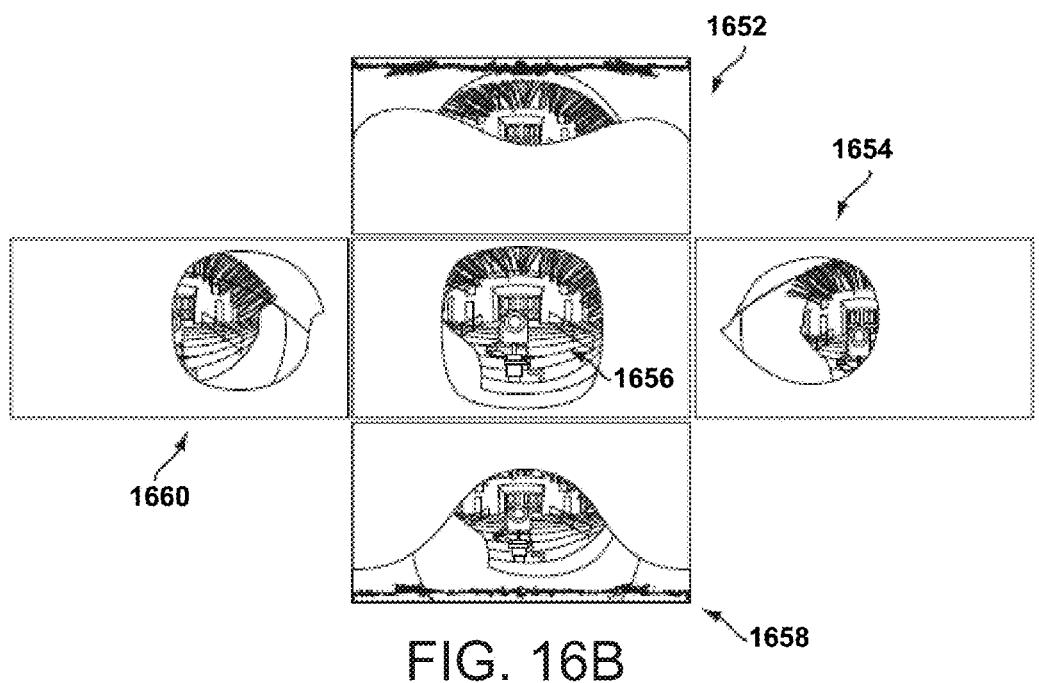
FIG. 16B is an illustration of reflected images corresponding to the eye positions shown in FIG. 6A, according to an exemplary embodiment.

For example, FIG. 16A is an illustration of a number of eye positions, according to an exemplary embodiment. Further, FIG. 16B is an illustration of reflected images corresponding to the eye positions shown in FIG. 16A, according to an exemplary embodiment. In particular, reflected image 1652 illustrates the image reflected from the cornea when the eye is in position 1602, reflected image 1654 illustrates the image reflected from the cornea when the eye is in position 1604, reflected image 1656 illustrates the image reflected from the cornea when the eye is in position 1606, reflected image 1658 illustrates the image reflected from the cornea when the eye is in position 1608, and reflected image 1660 illustrates the image reflected from the cornea when the eye is in position 1610. Further, as shown in FIG. 16B, reflected images 1652 to 1660 may match up with areas 1502 to 1510, respectively, on spherical panorama 1500 of FIG. 15.

As such, a spherical panorama 1500 may provide an environmental map that can be used to generate an expected end state of the reflected image if the only movement of the eye were due to head movement. To do so, the HMD may first determine the initial observed state of the reflected image. The HMD may then determine the area in the spherical panorama that corresponds to the initial observed state of the reflected image. As such, the HMD can use an ellipsoidal model of the eye to determine the expected position of the eye, assuming that the eye starts at the initial eye position and undergoes only the head-movement component of eye movement. The expected position of the eye may then be mapped to the spherical panorama 1500 to determine how the reflected image is expected to look after only the head-movement component of eye movement.

For example, consider a scenario where the initially observed state of the eye is represented by reflected image 1654. In this scenario, the HMD may match reflected image to area 1604 on spherical panorama 1500. Then, based on the predetermined mapping of eye position to locations in spherical panorama 1500, the HMD may determine that the expected end state of the reflected image is represented by area 1506 in spherical panorama 1500 (e.g., the end state corresponding to a movement from eye position 1604 to eye position 1606). Accordingly, area 1506 may be defined as the expected end state of the reflected image, and thus may serve as an indication of the movement during the period for which the eye movement is being determined.

Additionally or alternatively, optical-flow and/or feature mapping techniques may be used to determine the expected movement of the reflected image. For example, the HMD may flatten the initially taking known distances to reflected features in a reflected image, the HMD may determine an optical flow and/or a feature map of the reflected features, from the initially observed state of the reflected, which is expected to occur based on only the head-movement component of eye movement.

H. Determining the Second Eye-Movement Component

In an exemplary embodiment, the second-eye movement component may be a measure of orbital eye movement; or in other words, movement of the eye relative to the orbit (i.e., the "eye socket"), which is caused by the muscles controlling the eye. Thus, the combination of the second eye-movement component, which indicates how much the eye has moved within the orbit, and the first eye-movement component, which indicates how much the eye has moved due to head movement, may indicate the overall movement of the eye in space. (Note that determining of the orbital eye movement may be the general purpose of an exemplary method.)

Figure 16C:
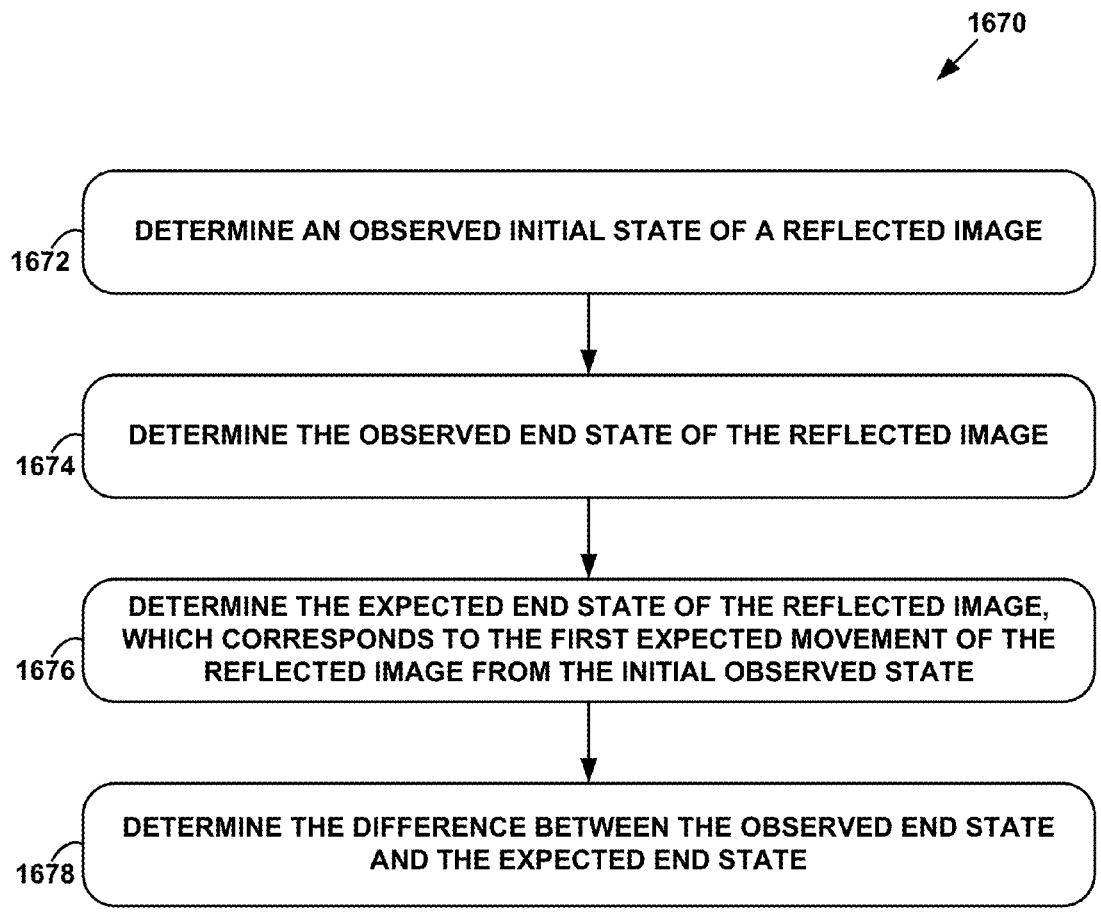
FIG. 16C is a flow chart illustrating a method for determining the second eye-movement component, according to an exemplary embodiment.

In order to estimate the orbital eye movement, an HMD may compare the observed state and the expected state at the end of the predetermined period. More specifically, FIG. 16C is a flow chart illustrating a method 1670 for determining the second eye-movement component, according to an exemplary embodiment.

As shown by block 1672, method 1670 involves the HMD determining an observed initial state of a reflected image (e.g., the observed state at the start of the predetermined period). The HMD then determines the observed end state of the reflected image (e.g., the observed state at the end of the predetermined period), as shown by block 1674. Further, the HMD determines an indication of the expected eye-movement, given that the only eye movement results from head movement. They HMD may do so by determining the expected end state of the reflected image, which corresponds to the first expected movement of the reflected image from the initial observed state, as shown by block 1676. The HMD then determines the difference between the observed state and the expected state at the end of the predetermined period, as shown by block 1678.

In an exemplary embodiment, orbital eye movement may be assumed to be the reason for this difference. Therefore, the amount of eye-movement that accounts for the difference between the observed end state and the expected end state of the reflected image may serve as an estimate of the orbital eye movement. Thus, in an exemplary embodiment, the second eye-movement component may be an estimate of orbital eye movement that is determined using a technique such as that illustrated by method 1670.

For example, referring back to FIGS. 15, 16A, and 16B, consider the scenario described above where the expected end state of the reflected image is reflected image 1656, which corresponds to area 1506 in panorama 1500. If the observed end state of the reflected image is reflected image 1660, for example, then the estimated orbital eye movement is the eye movement that accounts for the difference between the observed and expected, assuming that the head-movement component of eye movement has been correctly determined. For instance, given if reflected image 1660 is the observed end state and reflected image 1656 is the expected end state, then the estimated orbital eye movement corresponds to a movement from eye position 1606 to eye position 1610 (e.g., between area 1506 and area 1510 in panorama 1500).

Optical flow and/or feature mapping may also be used here to determine the orbital component of eye movement. For example, the HMD may start with the expected end state of the reflected image after head movement and the observed end state, which may take the form of images that are represented on the ellipsoidal surface of the cornea. As such, the HMD may flatten the expected end state image and the observed end state image, and determine optical flow and/or perform feature mapping between the flattened images. This optical flow may serve as the estimation of the orbital eye movement. Additionally or alternatively, the optical flow and/or feature map may be mapped back to the 3D ellipsoidal model of the corneal surface. Doing so may provide an estimation of orbital eye movement on the corneal surface and/or provide an indication of the ending position of the eye.

I. Determining the Expected Movement of the Reflected Image Corresponding to the Combination of the First and Second Eye-Movement Components After estimating the head-movement component (e.g., the first eye-movement component) and orbital component (e.g., the second eye-movement component) of the overall eye movement, the HMD may determine a second expected movement of the reflected image, which, in an exemplary embodiment, corresponds to the combination of head-movement component of eye movement and the orbital eye-movement estimate. More specifically, the head-movement component of eye movement and the orbital eye-movement estimate may be combined to estimate an overall eye movement in space. The HMD may then calculate the expected movement of the reflected image, assuming the overall eye movement is correct.

In an exemplary embodiment, the expected movement of the reflected image that corresponds to the overall eye movement may be determined using similar techniques to those used when determining the expected movement of the reflected image based on only the head-movement component. However, other techniques may be utilized without departing from the scope of the invention.

Here, optical flow and/or image mapping may be used in a similar manner as described above with respect to determining the expected movement of the reflected image based on only head movement, except that here, the expected movement may account for the head-movement component and the orbital component of eye movement.

J. Determine a Difference Between the Observed Movement and the Second Expected Movement of the Reflected Image After determining the expected movement of the reflected image that corresponds to the overall eye movement, the HMD may compare the expected movement to the observed movement. To do so, the HMD may utilize similar techniques as when determining the difference between the observed movement and the expected movement based on only the head-movement component of eye movement.

For example, the HMD may again compare the observed state at the end of the predetermined period to the expected state at the end of the period for which eye movement is being determined. In particular, the HMD may compare the reflected image that is observed at the end of the period to an estimate of the reflected image that is generated from the panorama, based on eye undergoing the overall eye movement as determined, from the initially observed state of the reflected image.

At this point, the difference (if any) may be attributed to error in currently determined head-movement component of eye movement. Accordingly, the HMD may make appropriate adjustments, re-determine the head-movement component of eye movement, and repeat the exemplary method.

In a further aspect, optical flow and/or image mapping may be used in a similar manner as described above with respect to determining difference between the expected movement of the reflected image based on only head movement and the observed movement of the reflected image. However, in this case, the difference may be determined between the observed movement and the expected eye movement of the reflected feature that corresponds to the combination of the head-movement component and the orbital component of eye movement.

K. Recursively Adjusting the First Eye-Movement Component to Determine Eye Movement When the orbital eye movement has been correctly determined, the expected movement of the reflected image should be the same as or very close to the observed movement of the reflected image. In other words, the expected end state of the reflected image given the overall eye movement will match or nearly match the observed end state of the reflected image. Thus, determine whether the difference between the observed movement of the reflected image and the expected movement based on the overall eye movement is small enough to conclude that the orbital eye movement estimation can be set as the orbital eye movement for the time period being evaluated.

If the difference is too great (e.g., greater than a threshold difference), then the HMD may make various adjustments to affect the first eye-movement components. In an exemplary embodiment, the adjustments may be determined according to the difference between the observed and expected movement of the reflected image. In particular, the HMD may make adjustments in an effort to reduce the difference between the observed movement of the reflected image and the expected movement of the reflected image (e.g. in an effort to make the expected end state of the reflected image closer to matching the observed end state).

More specifically, if the expected movement the reflected image is greater than the observed movement, this may be interpreted to mean that the head-movement component of eye movement was likely over-estimated. Accordingly, adjustments may be made in an effort to reduce the head-movement component. Similarly, if the expected movement the reflected image is greater than the observed movement, this may be interpreted to mean that the head-movement component of eye movement was likely under-estimated. Accordingly, adjustments may be made in an effort to increase the head-movement component.

Further, the amount by which the adjustments are expected to affect the head-movement component may also be based on the difference between the observed and expected movement of the reflected image. For instance, in an exemplary embodiment, the HMD may make adjustments that are expected to make the observed and expected eye movement closer to one another, but are less than what would cause the expected movement to equal the observed movement. For example, the value of the one or more parameters may be adjusted such that the difference would be expected to decrease by 5% and 10%. Other examples are also possible. By adjusting the parameters gradually, an exemplary method may help to avoid a situation where the adjustment overshoots the required adjustments and potentially prevents successful assessment of eye movement.

In an exemplary embodiment, various adjustments may be made in an effort to increase or decrease the head-movement component of eye movement. For example, the HMD may adjust the manner in which raw movement data from sensors on the HMD is mapped to corresponding movement of the eye. To do so, the HMD may adjust the model of the human body and/or the model of the way the HMD sits in relation to the head when worn. Such an adjustment may involve an adjustment to the spatial relationship between the one or more sensors and the eye, an adjustment to the spatial relationship between the one or more sensors and the axes of head movement, and/or an adjustment to the spatial relationship between the axes of head movement and the eye and re-determining the first expected movement of the reflected image based on the re-determined first eye-movement component.

Once such adjustments are made, the HMD may re-determine the amount of eye movement caused by head movement, and repeat an exemplary method with the re-determined head-movement component. Further, the HMD may recursively repeat this process until the difference between the observed movement of the reflected image and the expected movement based on the overall eye movement is small enough to conclude that the orbital eye movement estimation can be set as the orbital eye movement for the time period being evaluated.

L. Pre-Mapping Reflected Features

As noted, some embodiments may utilize a spherical panorama to provide an environment map against which reflected images can be compared and matched to help determine eye position and/or movement. Accordingly, an exemplary method may further involve an initial process by which such a spherical panorama is created. A spherical panorama of stitched together corneal images may be generated with techniques such as those described in Hammoud, pages 170-173.

In a further aspect, an exemplary method may also involve determining the locations of reflected features in the spherical panorama, before performing functions such as those illustrated in method 1000 of FIG. 10. For example, to determine the distance from the eye to a reflected feature (referred to herein as the "z-distance"), an expectation maximization process may be performed. In an exemplary embodiment, a wearable computer may initiate the expectation maximization process with the initial assumption that the distance to a reflected feature is infinite and that the head of the wearer is not moving substantially. (Note that the wearable computer may use a gyroscope and/or an accelerometer to verify that the wearer is not moving their head.) With these assumptions, the wearable computer may be configured to determine the z-distance to the source of a reflected feature by comparing an observed movement of the reflected feature on the eye, to an expected movement that is based on an estimated z-distance, and adjusting the estimate of the z-distance until the observed movement of the reflected feature on the eye matches (or differs by less than a certain threshold from) the expected movement.

VI. Conclusion

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A computer-implemented method comprising:
    carrying out two or more eye-tracking processes that each provide eye-position data, wherein the eye-position data from each eye-tracking process indicates positioning of the eye over time, wherein the two or more eye-tracking processes comprise at least an ambient-glint eye-tracking process and a second eye-tracking process, wherein the ambient-glint eye-tracking process determines eye-position data based on one or more reflections of light from the eye that correspond to one or more light sources at one or more unknown locations, and wherein the eye tracking based on ambient glints determines the eye-position data using an expectation maximization process that alternatingly estimates a head-movement component and an orbital component of an observed eye movement until a combination of the estimated head-movement component and the estimated orbital component differ from an observed movement of the eye in space by less than a threshold amount;
    determining a reliability indication for at least one of the eye-tracking processes;
    determining a respective weighting value for each of two or more of the eye-tracking processes based at least in part on the reliability indication;
    determining a combined eye position based on a weighted combination of respective eye-position data that is concurrently available from the two or more eye-tracking processes, wherein the eye-position data from each eye-tracking process is weighted by the respectively determined weighting value for the eye-tracking process; and
    instructing a computing device to utilize the combined eye position for one or more functions that incorporate eye-position data.

2. The method of claim 1, wherein the reliability indication is a first reliability indication, the method further comprising:
   determining a second reliability indication for at least one of the eye-tracking processes;
   re-determining the respective weighting value for each of the eye-tracking processes based at least in part on the second reliability indication; and
   re-determining the combined eye position based on a weighted combination of eye-position data in which the eye-position data from each eye-tracking process is weighted by respectively determined weighting value for the eye-tracking process.

3. The method of claim 1, wherein the two or more eye-tracking processes comprise two or more of: (a) eye-tracking based on controlled glints, (b) limbus tracking, (c) the eye-tracking based on ambient glints, (d) pupil tracking, and (e) eye-tracking with inward-facing proximity sensors.

4. The method of claim 1, wherein the method is carried out by a head-mountable display (HMD).

5. The method of claim 4, further comprising:
   causing a camera that is attached to a head-mounted display (HMD) to record a video of the eye;
   wherein carrying out the two or more eye-tracking processes comprises analyzing the video of the eye to determine input data for the two or more eye-tracking processes.

6. The method of claim 1, wherein the method of claim 1 is periodically repeated in order to dynamically switch between the eye-tracking process based on ambient glints and at least one other eye-tracking process such that the ambient-glint eye-tracking process is utilized when the at least one other eye-tracking process is determined to be unreliable.

7. The method of claim 6:
   wherein the two or more eye-tracking processes comprise at least: (a) eye-tracking based on controlled glints, (b) limbus tracking, and (c) the eye-tracking based on ambient glints, and wherein the method of claim 1 is periodically repeated in order to dynamically switch between the controlled-glint eye-tracking process, the limbus-tracking process, and the ambient-glint eye-tracking process.

8. The method of claim 7, wherein determining the combined eye position comprises:
   if the controlled-glint eye-tracking process is determined to be reliable, then using the eye-position data from the controlled-glint eye-tracking process; and
   if the controlled-glint eye-tracking process is determined to be unreliable, then:
      if the limbus-tracking process is also determined to be reliable, then using eye-position data from the limbus-tracking process; and
      if the limbus-tracking process is also determined to be unreliable, then using eye-position data from the ambient-glint eye-tracking process.

9. The method of claim 7, wherein determining the combined eye position comprises:
   if the limbus-tracking process is determined to be reliable, then using eye-position data from the limbus-tracking process; and
   if the limbus-tracking process is determined to be unreliable, then:
      if the controlled-glint eye-tracking process is determined to be reliable, then using the eye-position data from the controlled-glint eye-tracking process; and
      if the controlled-glint eye-tracking process is also determined to be unreliable, then using eye-position data from the ambient-glint eye-tracking process.

10. The method of claim 9, wherein the default weighting value for ambient-glint eye-tracking is zero.

11. The method of claim 9, wherein the second eye-tracking process comprises eye-tracking based on controlled glints, and wherein determining the reliability indication for at least one of the eye-tracking processes comprises:
   analyzing a video of the eye to detect controlled glints upon which to base the controlled-glints eye-tracking process;
   determining a spatial relationship between the controlled glints that are detected in the video;
   determining a difference between the determined spatial relationship and a model-based spatial relationship of the controlled glints, wherein the model-based relationship is based on a model of the human eye and positioning of light sources of the controlled glints relative to the eye.

12. The method of claim 9, wherein one of the eye-tracking processes comprises a limbus-tracking process, and wherein determining the reliability indication for at least one of the eye-tracking processes comprises:
   analyzing a video of the eye to detect a limbus of the eye; and
   determining that a certain portion of the limbus is captured in the video.

13. The method of claim 12, wherein determining the respective weighting value for each of the eye-tracking processes comprises determining the weighting value for at least the limbus-tracking process based at least in part on the portion of the limbus that is captured in the video.

14. The method of claim 9, wherein one of the eye-tracking processes comprises eye-tracking based on controlled glints, and wherein determining the reliability indication for at least one of the eye-tracking processes comprises:
   analyzing a video of the eye to detect controlled glints upon which to base the controlled-glints eye-tracking process; and
   determining that the video does not provide controlled glints that are suitable for the controlled-glints eye-tracking process.

15. The method of claim 14, wherein the weighting value for the ambient-glint eye-tracking process is equal to a first weighting value immediately before determining that the video does not provide suitable controlled glints, and wherein determining the respective weighting value for each of the eye-tracking processes comprises:
   in response to the determination that the video does not provide suitable controlled glints for the controlled-glints eye-tracking process, determining a second weighting value for the ambient-glint eye-tracking process, wherein the second weighting value is greater than the first weighting value.

16. The method of claim 9, wherein one of the eye-tracking processes comprise a limbus-tracking process, and wherein determining the reliability indication for at least one of the eye-tracking processes comprises:
   analyzing a video of the eye to detect a limbus of the eye; and
   determining that the video does not capture at least a portion of the limbus that is suitable for the limbus-tracking process.

17. The method of claim 16, wherein the weighting value for the ambient-glint eye-tracking process is equal to a first weighting value immediately before determining that the video does not capture a suitable portion of the limbus, and wherein determining the respective weighting value for each of the eye-tracking processes comprises:
   in response to the determination that the video does not capture at least a portion of the limbus that is suitable for the limbus-tracking process, determining a second weighting value for the ambient-glint eye-tracking process, wherein the second weighting value is greater than the first weighting value.

18. The method of claim 6, wherein one of the eye-tracking processes is eye-tracking based on controlled glints, and wherein carrying out eye-tracking based on controlled glints comprises:
   analyzing the video of the eye to detect controlled glints that correspond to the plurality of light sources; and
   determining eye-position data based on the controlled glints.

19. The method of claim 18, wherein determining the respective weighting value for each of the eye-tracking processes comprises determining the weighting value for the controlled-glint eye-tracking process based at least in part on the difference between the determined spatial relationship and a model-based spatial relationship of the controlled glints.

20. The method of claim 6, wherein carrying out eye-tracking based on ambient glints comprises:
   analyzing the video of the eye to detect one or more ambient glints that correspond to one or more light sources; and
   determining eye-position data based on the ambient glints.

21. The method of claim 1, wherein a default weighting for the eye-tracking processes specifies that a default weighting value for the ambient-glint eye-tracking is less than the weighting value for each of the one or more other eye-tracking process.

22. A wearable device comprising:
   at least one inward-facing image capture device arranged to capture image data that includes reflections of light from the eye that correspond to one or more light sources at one or more unknown locations;
   a non-transitory computer-readable medium; and
   program instructions stored on the non-transitory computer-readable medium and executable by at least one processor to:
      perform two or more eye-tracking processes that each provide eye-position data, wherein the eye-position data from each eye-tracking process indicates positioning of the eye over time, wherein the two or more eye-tracking processes comprise at least an ambient-glint eye-tracking process and a second eye-tracking process, wherein the ambient-glint eye-tracking process determines eye-position data based at least in part on the one or more reflections of light from the eye that correspond to one or more light sources at one or more unknown locations, and wherein the eye tracking based on ambient glints determines the eye-position data using an expectation maximization process that alternatingly estimates a head-movement component and an orbital component of an observed eye movement until a combination of the estimated head-movement component and the estimated orbital component differ from an observed movement of the eye in space by less than a threshold amount;
      determine a reliability indication for at least one of the eye-tracking processes;
      determine a respective weighting value for each of the eye-tracking processes based at least in part on the reliability indication;
      determine a combined eye position based on a weighted combination of respective eye-position data that is concurrently available from the two or more eye-tracking processes, wherein the eye-position data from each eye-tracking process is weighted by the respectively determined weighting value for the eye-tracking process; and
      instruct a computing device to carry out functions based on the combined eye position.

* * * * *